United States Patent [19]

Christensen et al.

[11] 4,347,368
[45] Aug. 31, 1982

[54] 3-SUBSTITUTED-6-SUBSTITUTED-7-OXO-1-AZABICYCLO[3.2.0]HEPT-2-ENE-2-CARBOXYLIC ACID

[75] Inventors: Burton G. Christensen, Scotch Plains; David B. R. Johnston, Warren; Susan M. Schmitt, Scotch Plains, all of N.J.

[73] Assignee: Merck & Co., Inc., Rahway, N.J.

[21] Appl. No.: 207,042

[22] Filed: Nov. 14, 1980

Related U.S. Application Data

[63] Continuation-in-part of Ser. No. 134,381, Mar. 27, 1980, abandoned, which is a continuation-in-part of Ser. No. 933,681, Aug. 17, 1978, abandoned, which is a continuation-in-part of Ser. No. 843,378, Oct. 19, 1977, abandoned.

[51] Int. Cl.³ ............................................. C07D 487/04
[52] U.S. Cl. .............................. 546/272; 260/239 A; 260/245.2 T; 260/245.3; 424/258; 424/263; 424/269; 424/270; 424/272; 424/273 B; 424/274; 542/413; 542/443
[58] Field of Search ................. 260/245.2 T; 546/272; 542/413, 443

[56] References Cited

U.S. PATENT DOCUMENTS 4,232,036 11/1980 Christensen et al. ........ 260/245.2 T
4,234,596 11/1980 Christensen et al. ........ 260/245.2 T
4,264,621 4/1981 Christensen et al. ........ 260/245.2 T
4,269,873 5/1981 Christensen et al. ........ 260/245.2 T
4,281,002 7/1981 Christensen et al. ........ 260/245.2 T Primary Examiner—Mary C. Lee
Attorney, Agent, or Firm—James A. Arno; Hesna J. Pfeiffer

[57] ABSTRACT

Disclosed are 3- and 6-substituted 7-oxo-1-azabicyclo[3.2.0]hept-2-ene-2-carboxylic acids having the structure:

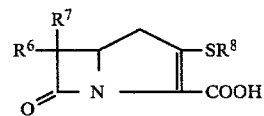

wherein $R^6$, $R^7$ and $R^8$ are, inter alia, independently selected from the group consisting of hydrogen, alkyl, alkenyl, aryl and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

2 Claims, No Drawings

3-SUBSTITUTED-6-SUBSTITUTED-7-OXO-1-AZABICYCLO[3.2.0]HEPT-2-ENE-2-CARBOXYLIC ACID

BACKGROUND OF THE INVENTION

This application is a continuation-in-part of U.S. Patent Application Ser. No. 134,381 filed Mar. 27, 1980, now abandoned which is a continuation-in-part of U.S. Patent Application Ser. No. 933,681 filed Aug. 17, 1978, now abandoned; which in turn is a continuation-in-part of U.S. Patent Application Ser. No. 843,378 filed Oct. 19, 1977, now abandoned.

This invention relates to 3- and 6-substituted-7-oxo-1-azabicyclo[3.2.0]hept-2-ene-2-carboxylic acids and derivatives thereof which are useful as antibiotics and which may be represented by the following generic structural formula (I):

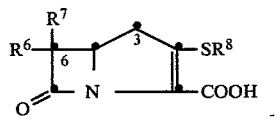

wherein $R^6$, $R^7$ and $R^8$ are independently selected from the group consisting of hydrogen, substituted and unsubstituted: alkyl, alkenyl, and alkynyl, having from 1-10 carbon atoms cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the linear chain has 1-6 carbon atoms; heteroaryl, heteroaralkyl, heterocyclyl and heterocyclylalkyl wherein the substituent or substituents relative to the above-named radicals are selected from the group consisting of: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxy; and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms.

This invention also relates to the carboxyl derivatives of I which are antibiotics and which may be represented by the following generic structure (I):

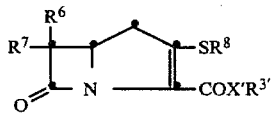

wherein $X'$ is oxygen, sulphur or $NR'$ ($R'$=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic μ-lactam antibiotic art; the definition of $R^{3'}$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus*, *Strep. pyogenes*, and *B. subtilis*, and gram negative bacteria such as *E. coli*, *Pseudomonas*, *Proteus morganii*, *Serratia* and *Klebsiella*. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

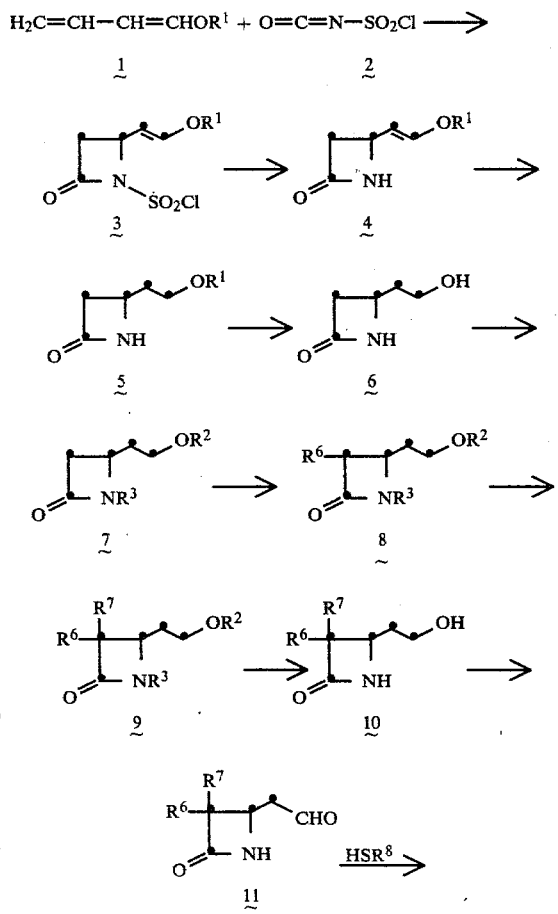

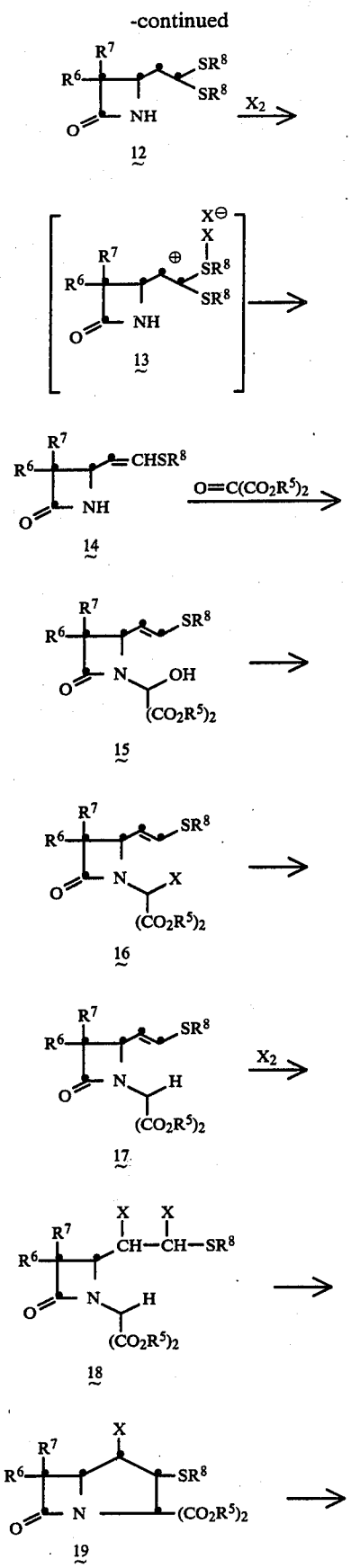

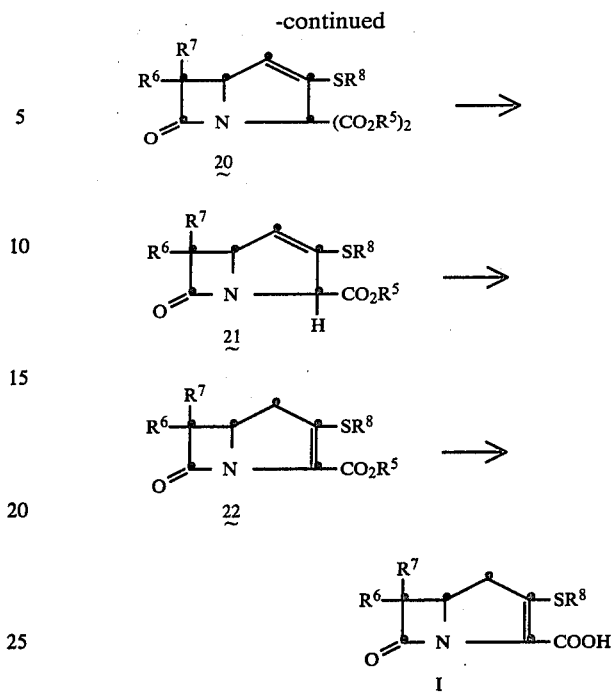

In words relative to the above diagram, the 4-(2-substituted-vinyl)azetidine-2-one, 4, starting material is prepared by reacting an $R^1$-oxybutadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical $R^1$ is an easily removable acyl blocking group such as alkanoyl or aralkanoyl which bears no functional group or groups which might interfere with the desired course of reaction (1+2→3→4). Intermediate species 3 is converted to the sulfinamide by reduction which is then hydrolyzed to 4 at pH 6–8. Typically the reaction solution comprising 3 is contacted (5–30 minutes) with an aqueous solution (at 0°–25° C.) of a reducing agent such as sodium sulfite, thiophenol, or the like, at pH 6–8 to provide 4.

The reaction 4→5 is a reduction, and is preferably achieved by hydrogenation in a solvent such as ethylacetate ether, dioxane, tetrahydrofuran (THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The de-blocking reaction 5→6 is usually desirable when $R^1$ is acyl to permit the later alkylation, 7→8. The preferred de-blocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from −10° to 25° C.

Blocking groups $R^3$ and $R^2$ are established (6→7) to provide a suitably protected species for alkylation (7→8→9). There is no criticality in the choice of blocking groups, provided only that they do not interfere with the intended alkylation. $R^3$ may be hydrogen, a triorganosilyl group such as trimethylsilyl or the like, or a cyclic ether such as 2-tetrahydropyranyl. $R^2$ may also be a cyclic ether such as 2-tetrahydropyranyl; alternatively R³ and R² may be joined together to form protected species such as 7a:

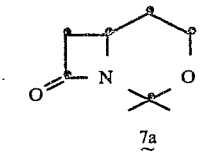

For example, species such as 7a are conveniently prepared by treating 6 with 2,2-dimethoxypropane in the presence of a catalyst such as boron trifluoride etherate, toluene sulphonic acid, or the like in a solvent such as methylene chloride, ether, chloroform, dioxane or the like at a temperature of from −10° C. to 35° C. for from a few minutes to 1 hour. Species 7 can be mono- or dialkylated at ring position 6. Alkylation of 7 provides 8. Typically, 7 is treated with a strong base such as lithium diisopropyl amide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, R⁶X, is added (R⁶ is as described above and X is chloro, iodo or bromo; alternatively the alkylating agent may be R⁶-tosylate, R⁶-mesylate or an aldehyde or ketone such as acetaldehyde and the like) to provide monoalkylated species 8. When desired dialkylated species 9 may be obtained from 8 by repeating the alkylating procedure, 7→8.

The de-blocking reaction 9→10 is typically conducted by acid hydrolysis such as aqueous acetic acid at a temperature of from 25° C. to 75° C. for from 5 minutes to 3 hours.

The aldehyde intermediate 11 is prepared by treating 10 with an oxidizing agent such as CrO₃.2 (pyridine) in CH₃CN, 1:1 mixture of dimethylsulfoxide and acetic anhydride, cyclohexylcarbodiimide in DMSO or the like at a temperature of from 0°-25° C. for from 5 minutes to 1 hour. The resulting species 11 in a solvent such acetonitrile, methylene chloride, chloroform or the like at a temperature of from −10° to 25° C. is treated with an excess of the reagent HSR⁸ in the presence of an acid catalyst such as boron trifluoride etherate, toluene sulphonic acid or the like to provide 12. Typically, the reaction requires from 1 to 60 minutes.

The vinyl sulphide 14 is obtained via intermediate 13 by treating 12 with a halogen such as chlorine or bromine (X=Cl or Br) in s solvent such as ether, methylene chloride, tetrahydrofuran, glyme or the like at a temperature of from −78° to 30° C. for from 1 to 30 minutes, followed immediately by treating with an olefin such as cyclohexane, isobutylene, or the like in the presence of base such as triethylamine, DBU, sodium hydride, or the like in a solvent such as DMF, glyme, THF, HMPA. The solution is held at −20° to 25° C. for from 1 to 8 hours to yield 14.

The vinyl sulphide species 14 is reacted with a diester of oxomalonic acid (or its monohydrate) to provide 15. There is no criticality as to the identity of the ester moiety, R⁵, of the oxomalonic acid. R⁵ may be a conventional, easily removable blocking group or it may be a pharmaceutically acceptable ester moiety. Suitable ester radicals R⁵ are p-nitrobenzyl, benzyl, o-nitrobenzyl, t-butyl, 2,2,2-trichloroethyl. The reaction 14→15 is typically conducted in a high boiling organic solvent such as benzene, toluene, cyclohexane, halo aromatic or the like at a temperature of from about 50° C. to reflux for from 0.5 to 6 hours.

The halogenation reaction 15→16 is typically conducted in a solvent such as THF, glyme, ether, methylene chloride, chloroform or the like in the presence of a halogenating agent such as thionyl chloride, phosphorous pentachloride or the like in the presence of base such as pyridine at a temperature of from −20° to 25° C. for from 5 minutes to 3 hours. The selective reduction of 15→17 via 16 is completed by treating 16 with tributylphosphine, triphenylphosphine or the like in aqueous DMF or similar aqueous systems involving dioxane, THF, glyme, DMSO, or acetone at a temperature of from about 0°-50° C. for from 10 minutes to 5 hours.

Species 17 is halogenated by the previous procedure (12→13), but omitting the addition of the cyclohexane or other olefin, to provide the dihalo species 18. Species 18 is treated with a base such as triethylamine, sodium hydride or potassium hydride in a solvent such as DMF, acetonitrile, methylene chloride, chloroform, glyme or the like at a temperature of from about −78° to 25° C. for 1 to 5 hours to provide 19. Species 19 is converted to 20 on treatment with a strong base such as 1,5-diazabicyclo[5.4.0]-undec-5-ene(DBU),1,5-diazabicyclo[3.4.0]non-5-ene(DBN), or the like in a solvent such as DMSO, acetone, chloroform, DMF, THF, glyme or the like or on treatment with AgF in pyridine at a temperature of from 0°-40° C. for from ¼ to 24 hours. The reaction 20→21 is conducted by treating 20 with an aromatic base such as pyridine, aqueous dimethylsulfoxide, s-collidine or lutidine, in the presence of a displacing agent such as lithium iodide, sodium chloride, lithium bromide, sodium bromide, or the like at a temperature of from about 80°-150° C. for from 15 minutes to 2 hours. An aqueous work up of the resulting reaction mixture provides 21. Isomerization of the double bond 21→22 is accomplished by treating 21 in a solvent such as DMF, DMSO, ethyl ether, THF, glyme, methylene chloride with a strong base such as diisopropylamine, DBU, DBN, or the like at a temperature of from 0° to about 25° C. for from a few minutes to 2 hours or until equilibrium has been established as determined by examination of sample aliquots by ultraviolet absorption or by thin layer chromatography. The final reaction 22→I (hydrogenolysis of the blocking group) is accomplished by treating 22 in a solvent such as dioxane, ethanol, THF or the like or an aqueous mixture thereof in the presence of a Platinum metal catalyst such as Pd/C under a hydrogen pressure of from 1–4 atmospheres for from 0.5 to 8 hours at a temperature of from about 0°-25° C.

The above-described total synthesis may also advantageously start with 4-vinyl azetidinone[(23), below; E. J. Moriconi, W. C. Meyer, J. Org. Chem., 36, 2841(1971)] rather than the enol acylate azetidinone (4, above). This variation in the total synthesis has the advantage of conveniently imparting stereoselectivity to the process at an early stage. The following scheme illustrates this 4-vinyl azetidinone embodiment of the present invention; notice that it ties into the above scheme at species 14.

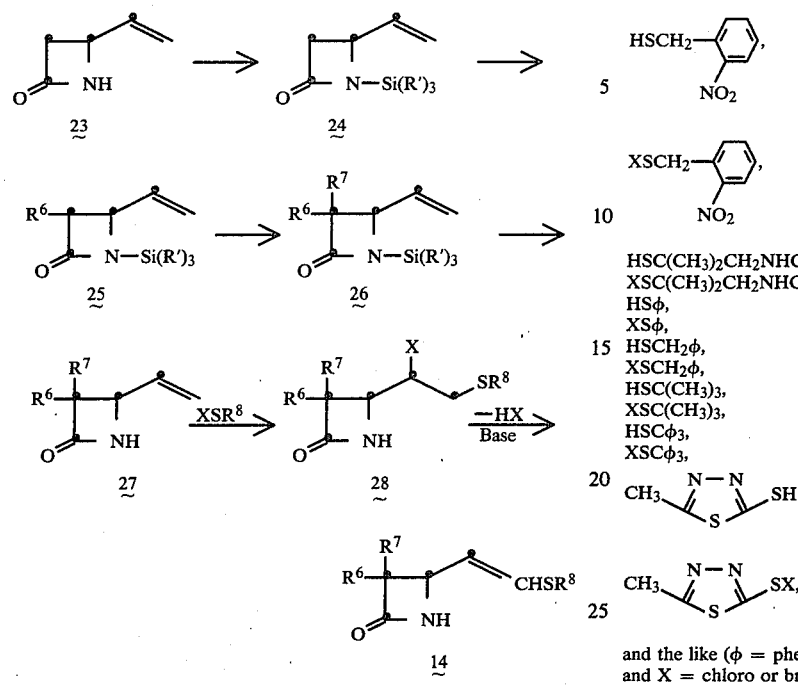

In words relative to the above reaction diagram, 4-vinyl azetidinone 23 is silylated to provide the N-silyl species 24. The groups R' on the silyl radical are lower alkyl having from 1-6 carbon atoms especially preferred triorganosilyl groups are trimethylsilyl and t-butyl-dimethylsilyl. Typically, the silylation (23→24) is achieved by treating 23 in a solvent such as DMF, DMSO, HMPA or the like with the silylating agent of choice, dimethyl t-butylsilyl chloride, and a base such as Et$_3$N, pyridine, N,N-dimethylaniline and the like at a temperature of from −10° to 30° C. for from 1 to 8 hours. Species 24 is alkylated to form 25 or 26 and this alkylation is conducted exactly as described above for the alkylation 7→8→9. It should be noted here that the reactions (24→25) and (25→26) represent convenient opportunities to separate species 25 and 26 into their racemic diastereoisomers if desired. The removal of the N-triorganosilyl group is accomplished in reaction 26→27 by mild acid catalyzed solvolysis. The halo sulfide species 28 is obtained from 27 by treating 27 in a solvent such as methylene chloride, THF, glyme, or the like with the reagent XSR$^8$ wherein R$^8$ has previously been defined and X is halogen such as chloro or bromo at a temperature of from −50° to 50° C. for from 1 to 16 hours. The vinyl sulfide intermediate 14, which is common to the above illustrated scheme of total synthesis is obtained from 28 by elimination of HX on treatment of 28 with a base such as 1,5-diazabicyclo[5.4.0]undec-5-ene (DBU), 1,5-diazabicyclo[4.3.0]non-5-ene, (DBN), 1,4-diazabicyclo[2.2.2]octane, (DABCO), or silver fluoride in a solvent such as DMSO, pyridine DMF, HMPA or the like at a temperature of from −20° to 50° C. for from ¼ to 16 hours.

In the foregoing description of the invention, suitable reagents HSR$^8$ (11→12) and XSR$^8$ (27→28) are representatively illustrated by the following list:

HSCH$_2$CH$_2$CH$_2$NHCO$_2$PNB,
PNBO$_2$CNHCH$_2$CH$_2$CH$_2$SX,

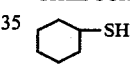

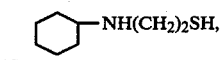

HSC(CH$_3$)$_2$CH$_2$NHCO$_2$PNB,
XSC(CH$_3$)$_2$CH$_2$NHCO$_2$PNB,
HSφ,
XSφ,
HSCH$_2$φ,
XSCH$_2$φ,
HSC(CH$_3$)$_3$,
XSC(CH$_3$)$_3$,
HSCφ$_3$,
XSCφ$_3$,

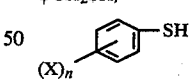

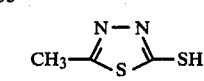

and the like (φ = phenyl; PNB = p-nitrobenzyl and X = chloro or bromo).
CH$_3$SH,
CH$_3$CH$_2$SH,
CH$_3$(CH$_2$)$_2$SH
(CH$_3$)$_2$CHSH,
CH$_3$(CH$_2$)$_3$SH,
(CH$_3$)$_2$CH(CH$_2$)$_2$SH,
CH$_2$=CHCH$_2$SH,
CH≡CCH$_2$SH,

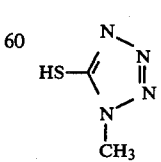

φ(CH$_2$)$_3$SH(φ = PHENYL),
φ(CH$_2$)$_2$SH,
HO(CH$_2$)$_2$SH,
H$_2$N(CH$_2$)$_2$SH,
H$_2$N(CH$_2$)$_3$SH,
CH$_3$(CH$_2$)$_2$NH(CH$_2$)$_2$SH, (CH$_3$)$_2$N(CH$_2$)$_2$SH,
(CH$_3$CH$_2$)$_2$N(CH$_2$)$_2$SH,
HO$_2$C(CH$_2$)$_2$SH,
φCH$_2$SH, (n = 0, 1 or 2; X = Cl, Br, F, Cl, OCH$_3$, CH$_3$NH$_2$,
$$\overset{O}{\underset{\|}{NHCCH_3}}),$$

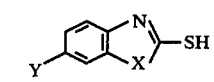

(when X = N, O, S, Y = H; when X = S, Y = H, OCH₂CH₃, Cl)

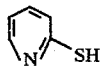

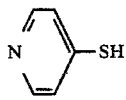

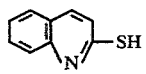

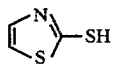

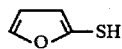

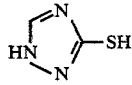

Similarly, suitable alkylating agents for establishing R⁶ and/or R⁷ at ring position 6 (7→8→9) are:
φCH₂CHO,
φCH₂CH₂CHO,
CH₂O,
CH₃I,
φCH Br,
CH₃COCH₃.

As noted above, the compounds of the present invention may also generally be represented by the following structural formula:

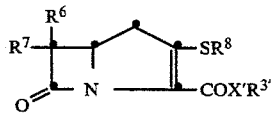

I wherein X' is oxygen, sulfur or NR' (R' is hydrogen or loweralkyl having from 1 to 6 carbon atoms); and R³' is hydrogen, or, inter alia, is representatively selected to provide the pharmaceutically acceptable salt, ester anhydride (R³' is acyl) and amide moieties known in the bicyclic β-lactam antibiotic art.

Identification of the Radical —COX'R³'

In the generic representation of the compounds of the present invention (I, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and the nuclear analogues thereof.

Suitable radicals (R³' include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups, wherein X'=O and R³' is given:

(i) R³'=CRᵃRᵇRᶜ wherein at least one of Rᵃ, Rᵇ and Rᶜ is an electron-donor, e.g., p-methoxyphenyl. The remaining Rᵃ, Rᵇ and Rᶜ groups may be hydrogen or organic substituting groups. Suitable ester groups of this type include p-methoxybenzyloyxcarbonyl.

(ii) R³'=CRᵃRᵇRᶜ wherein at least one of Rᵃ, Rᵇ and Rᶜ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) R³'=CRᵃRᵇRᶜ wherein at least two of Rᵃ, Rᵇ and Rᶜ are hydrocarbon such as alkyl, e.g., methyl or ethyl, or aryl, e.g., phenyl and the remaining Rᵃ, Rᵇ and Rᶜ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: R⁴₃SiX' wherein X' is a halogen such as chloro or bromo and R⁴ is alkyl, e.g., methyl, ethyl, t-butyl.

More generally stated, pharmaceutically acceptable carboxyl derivatives of the present invention are those derived by reacting I with alcohols, acylating reagents and the like. For example, esters and amides of interest are the above-listed starting materials and final products having the —COX'R³' group at the 2-position; wherein X' is oxygen, sulfur or NR' (R' is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the $$\begin{array}{c} R' \\ | \\ -N- \end{array} \text{group.}$$

Representative of such amides are those wherein R' is selected from the group consisting of hydrogen and lower alkyl such as methyl and ethyl.

The most preferred —COX'R³' radicals of the present invention are those wherein (relative to Structure I above), X is oxygen and R is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkyl-amino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric tartaric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus the free acid, free base, and especially the salts thereof such as amine and metal salts, particularly the alkali metal and alkaline earth metal salts, are useful bactericides and can be used for removing susceptible pathogens from dental and medical equipment for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram positive or gram-negative bacteria, for example against *Staphylococcus aureus, Escherichia coli, Klebsiella pneumoniae, Bacillus subtilis, Salmonella typhosa, Pseudomonas* and *Bacterium proteus*. The antibacterials of the invention may further be utilized as additives to animal feeding-stuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention. All reaction temperatures are in °C.

EXAMPLE 1

Preparation of 4-(2-acetoxyvinyl)azetidinone-2-one $H_2C=CH-CH=CHOC-CH_3 + O=C=N-SO_2Cl \longrightarrow$
$\phantom{H_2C=CH-CH=CHO}\overset{\|}{\phantom{C}}$
$\phantom{H_2C=CH-CH=CHOC}O$

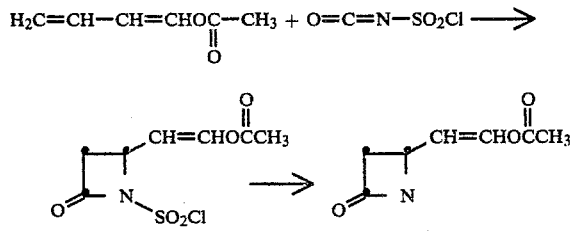

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 2.5 g 1-acetoxybutadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish-orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a $N_2$ stream. The product crystallizes from fractions 4–6, with traces in 3 and 7. Fractions 1–3 contain a yellowish sharp-smelling material which resinifies on standing. Yield: 100 mg as a mixture of the cis and trans isomers.

EXAMPLE 2

Preparation of 4-(2-Acetoxyethyl)-2-Azetidinone

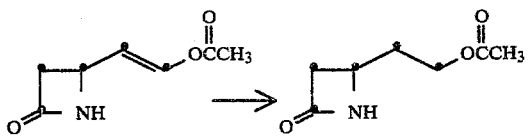

A solution of 4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-(2-acetoxyethyl)-2-azetidinone (10.0 g) as a crystalline solid. Recrystallization from ether affords white crystals: M.P. 44°–7°; ir $(CHCl_3)_\mu$ 5.66, 5.74; nmr $(CDCl_3)$ $\tau$3.44 (broad s, 1, NH), 5.82 (m, 2, $CH_2OCOCH_3$), 6.29 (m, 1, C-4H), 6.87 (½ AB pattern further split in four by C-4H and NH, 1, $J_{gem}=12.8$ Hz, $J=4.5$ H $J_{NH}=1.9$ Hz, 7.38 (½ AB pattern further split in four by C-4H and NH, 1, $J_{gem}=12.8$ Hz, $J=2.3$ Hz, $J_{NH}=1.0$ Hz), 7.93 and 8.02 (s, on m, total 5, $OCOCH_3$ and $CH_2CH_2OCOCH_3$, respectively).

EXAMPLE 3

Preparation of 4-(2-Hydroxyethyl)-2-Azetidinone

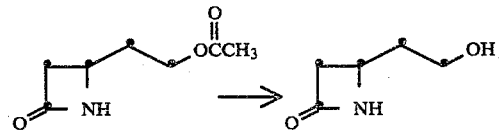

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/$CHCl_3$ to give 1.55 g of the alcohol: m.p. 50°; ir $(CHCl_3)$ $\mu$5.67; nmr $(CDCl_3)$ $\tau$3.20 (broad s, 1, NH), 6.24 and 6.28 (m on t, total 3, C-4H and CH$_2$OH respectively), 6.90 (broad s on ½ AB pattern further split in four by C-4H and NH, total 2, OH and C-3H respectively, J$_{gem}$=13.0 Hz, J$_{vic}$=4.2 Hz, J$_{NH}$=1.6 Hz), 7.42 (½ AB pattern further split in four by C-4H and NH, 1, C-3H, J$_{gem}$=13.0 Hz, J$_{vic}$=2.2 Hz, J$_{NH}$=1.1 Hz), 8.16 (m, 2, CH$_2$CH$_2$OH).

EXAMPLE 4

Preparation of 8-Oxo-2,2-dimethyl-3-oxa-1-azabicyclo [4.2.0]octane

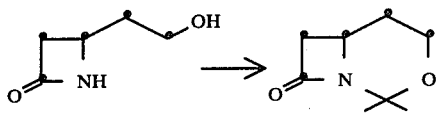

A solution of 4-(2-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]-octane (1.59 g) as a crystalline solid. Recrystallization from ether/hexane gives product of m.p. 60°-1°.

| | |
|---|---|
| ir (CHCl$_3$)μ: | 5.73 (β-lactam) |
| nmr (CDCl$_3$)γ: | 6.02–6.28, m, 2H, C-4 methylene |
| | 6.22–6.62, m, 1H, C-6 methine |
| | 6.90, dd, 1H, J$_{7,7}$ = 14Hz, J$_{6,7}$ = 4.5Hz C-7 proton cis to C-6H |
| | 7.47, dd, 1H, J$_{7,7}$ = 14Hz, J$_{6,7}$ = 2Hz C-7 proton trans to C-6H |
| | 7.82–8.68, m, 2H, C-5 methylene |
| | 8.23, s, 3H ⎫ |
| | 8.57, s, 3H ⎭ C-2 methyls |

EXAMPLE 4a

Preparation of 8-oxo-2,2-dimethyl-7α-isopropyl-3-oxa-1-azabicyclo[4.2.0]octane

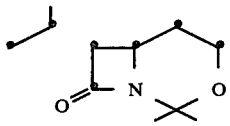

THF, 20 ml is placed under N$_2$, treated with 1.54 ml diisopropylamine and cooled to −78° C. A solution of n-butyl lithium 1.97 M in hexane 5.6 ml is added dropwise over 5 min. The reaction mixture is stirred at −78° C. for 10 min. and then treated with 8-oxo-2,2-dimethyl-3-oxa-1-azabicyclo[4.2.0]octane 1.55 g in 15 ml THF added dropwise over 5 min. After another 10 min. hexamethylphosphoramide 1.97 ml is added. The mixture is stirred another 10 min., then treated with 2 ml of isopropyl iodide. The reaction mixture is stirred at −78° C. for 15 min. and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C$_6$H$_6$ as eluant to give 8-oxo-2,2-dimethyl-7α-isopropyl-3-oxa-1-azabicyclo[4.2.0]-octane. μ i.r.: 5.7 (β-lactam). n.m.r. δ: 0.96d, 1.06d

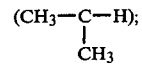

1.4S, 1.76S (gem dimethyl);
1.9m (C-5 H); 2.59d of d (C-7 H); 3.33m (C-6 H); 3.83d of d (C-4 H).

EXAMPLE 4b

Preparation of 8-oxo-2,2,7-trimethyl-3-oxa-1-azabicyclo[4.2.0]octane

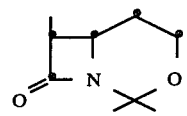

Following the procedure of Example 4a, except substituting an equivalent amount of methyl iodide for the isopropyl iodide, the title compound is obtained.

EXAMPLE 5

Preparation of 8-oxo-2,2,7-trimethyl-7-(hydroxymethyl)-3-oxa-1-azabicyclo[4.2.0]octane

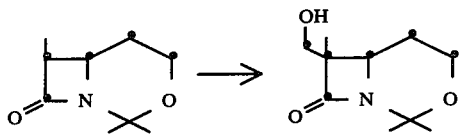

To a solution of 1.1 equivalents of freshly prepared lithium diisopropylamide in anhydrous tetrahydrofuran under a nitrogen atmosphere at −78° is added a solution of 8-oxo-2,2,7-trimethyl-3-oxa-1-azabicyclo-[4.2.0]octane in anhydrous tetrahydrofuran which has been cooled to −78° C. After two minutes, the resulting lithium enolate is treated with excess formaldehyde, introduced as a gas just above the surface of the stirred solution. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2,7-trimethyl-7-(hydroxymethyl)-3-oxa-1-azabicyclo[4.2.0]octane.

EXAMPLE 6

Preparation of 8-oxo-2,2,7-trimethyl-7-(p-nitrobenzyl-carbonyldioxymethyl)-3-oxa-1-azabicyclo[4.2.0]octane

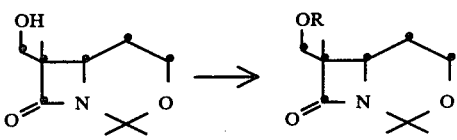

-continued

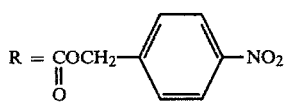

R = COCH₂—⟨phenyl⟩—NO₂ (with C=O)

Under anhydrous conditions at 0° C. a solution of 8-oxo-2,2,7-trimethyl-7-(hydroxymethyl)-3-oxa-1-azabicyclo[4.2.0]octane (60 mg., 0.302 mmole) in 0.6 ml ether is treated with powdered potassium hydroxide (19 mg, 0.332 mmole). After a period of 15 minutes, p-nitrobenzyl chloroformate (65 mg, 0.302 mmole) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure gives 67 mg of a colorless oil. Purification by preparative thick-layer chromatography on silica gel developing with 1:9 ethyl acetate/benzene gives 8-oxo-2,2,7-trimethyl-7-(p-nitrobenzylcarbonyldioxymethyl)-3-oxa-1-azabicyclo[4.2.0]octane (40 mg) as a mixture of diastereomers.

EXAMPLE 7

Preparation of 3-methyl-3-(p-nitrobenzylcarbonyldioxymethyl)-4-(2-hydoxyethyl)-2-azetidinone

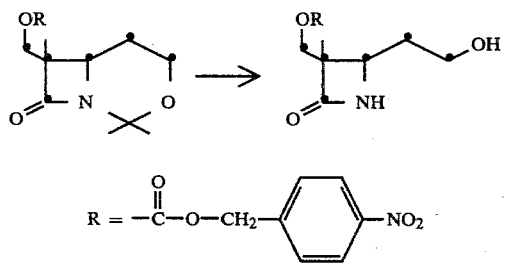

8-Oxo-3-oxa-2,2,7-trimethyl-7-(1-p-nitrobenzylcarbonyldioxymethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give 3-methyl-3-(p-nitrobenzylcarbonyldioxymethyl)-4-(2-hydroxyethyl)-2-azetidinone as a mixture of diastereoisomers.

EXAMPLE 8–11

Examples 8, 9, 10 and 11 as alternative to Examples 4, 5, 6 and 7 for the preparation of 3-methyl-3-(p-nitrobenzylcarbonyldioxymethyl)-4-(2-hydroxyethyl)-2-azetidinone

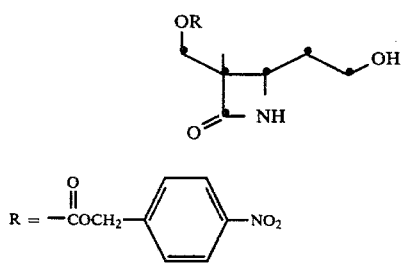

EXAMPLE 8

Preparation of 1-(2-Tetrahydropyranyl)-4-[2-(2-tetrahydropyranyl)oxyethyl]-2-azetidinone

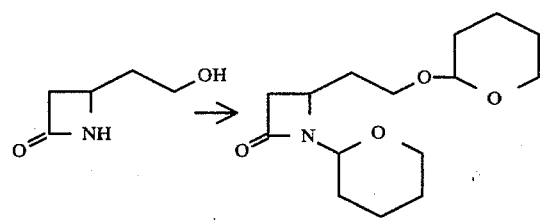

Under nitrogen and at 25° C., a solution of 4-(2-hydroxyethyl)-2-azetidinone (62 mg, 0.539 mmole) in 0.5 ml of anhydrous p-dioxane is treated with 2,3-dihydropyran (0.98 ml, 1.08 mmoles) and p-toluenesulfonic acid monohydrate (19 mg, 0.10 mmole). The resulting solution is stirred for a period of 60 minutes and then partitioned between 10 ml of 0.5 M pH7 phosphate buffer and 10 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give 216 mg of crude product. Purification by preparative thick-layer chromatography developing with ethyl acetate gives 80 mg of 1-(2-tetrahydropyranyl)-4-[2-(2-tetrahydropyranyl)oxyethyl]-2-azetidinone as an oil.

| nmr (CDCl₃)τ: | 5.13–5.60, m, OCH |
| | 5.83–6.85, m, C—4H + OCH₂ |
| | 6.95, dd, J = 5Hz and 15 Hz ⎫ C—3 methylene |
| | 7.35, dd, J = 3Hz and 15 Hz ⎭ |
| | 7.62–8.95, m, CHCH₂CH₂CH₂CH₂ + CHCH₂CH₂O |

The corresponding 3-methyl-1-(2-tetrahydropyranyl)-4-[2-(2-tetrahydropyranyl)oxyethyl]-2-azetidinone is obtained from the product of Example 4b via Examples 7.

EXAMPLE 9

Preparation of 1-(2-tetrahydropyranyl)-3-methyl-3-(1-hydroxymethyl)-4-[2-(2-tetrahydropyranyl)oxyethyl]-2-azetidinone

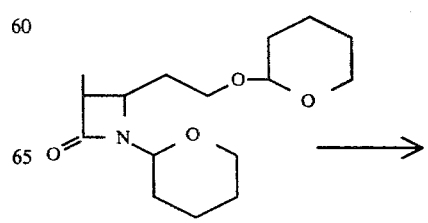

-continued

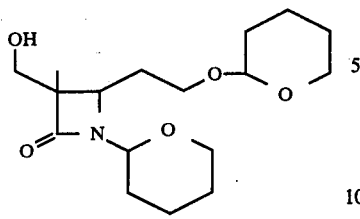

Following the procedure described for the preparation of 8-oxo-2,2,7-trimethyl-7-(hydroxymethyl)-3-oxa-1-azabicyclo[4.2.0]octane from 8-oxo-2,2,7-trimethyl-3-oxa-1-azabicyclo[4.2.0]octane (Example 5, above) and using 3-methyl-1-(2-tetrahydropyranyl)-4-[2-(2-tetrahydropyranyl)-oxyethyl]-2-azetidinone one obtains a diastereomeric mixture of 1-(2-tetrahydropyranyl)-3-methyl-3-(hydroxymethyl)-4-[2-(2-tetrahydropyranyl)oxyethyl]-2-azetidinone.

EXAMPLE 10

Preparation of 3-Methyl-1-(2-tetrahydropyranyl)-3-(1-p-nitrobenzylcarbonyldioxymethyl)-4-[2-(2-tetrahydropyranyl)oxyethyl]-2-azetidinone

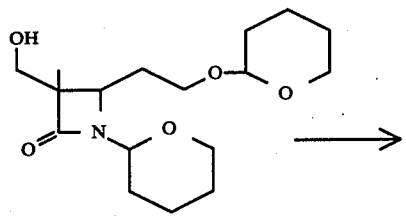

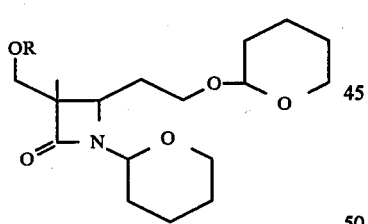

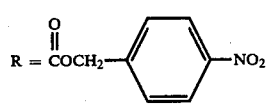

Following the procedure described for the preparation of 8-oxo-2,2,7-trimethyl-7-(1-p-nitrobenzylcarbonyldioxymethyl)-3-oxa-1-azabicyclo[4.2.0]octane from 8-oxo-2,2,7-trimethyl-7-(1-hydroxymethyl)-3-oxa-1-azabicyclo[4.2.0]octane and using 3-methyl-1-(2-tetrahydropyranyl)-3-(hydroxymethyl)-4-[2-(2-tetrahydropyranyl)oxyethyl]-2-azetidinone there is obtained 3-methyl-1-(2-tetrahydropyranyl)-3-(p-nitrobenzylcarbonyldioxymethyl)-4-([2-(2-tetrahydropyranyl)-oxyethyl]-2-azetidinone.

EXAMPLE 11

Preparation of 3-Methyl-3-(p-nitrobenzylcarbonyldioxyethyl)-4-(2-hydroxyethyl)-2-azetidinone

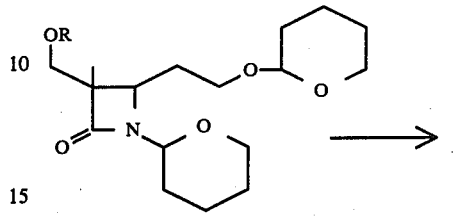

A solution of 3-methyl-1-(2-tetrahydropyranyl)-3-(p-nitrobenzylcarbonyldioxymethyl)-4-[2-(2-tetrahydropyranyl)-oxyethyl]-2-azetidinone in methanol at 25° C. is treated with 0.1 molar equivalent of p-toluenesulfonic acid monohydrate. The solution is stirred for a period of 2 hours and then neutralized with 1 M pH 7 phosphate buffer. The product is extracted into ethyl acetate. The ethyl acetate solution is washed with brine, dried over magnesium sulfate and filtered. The filtrate is evaporated under reduced pressure to give 3-methyl-3-(p-nitrobenzylcarbonyldioxymethyl)-4-(2-hydroxyethyl)-2-azetidinone.

EXAMPLE 12

Preparation of 3-(2-aminoethylthio)-6-methyl-6-(hydroxymethyl)-7-oxo-1-azabicyclo[3.2.0]hept-2-ene-2-carboxylic acid Step A

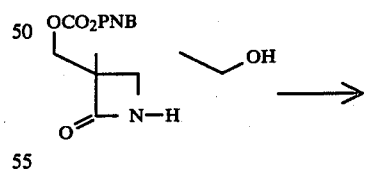

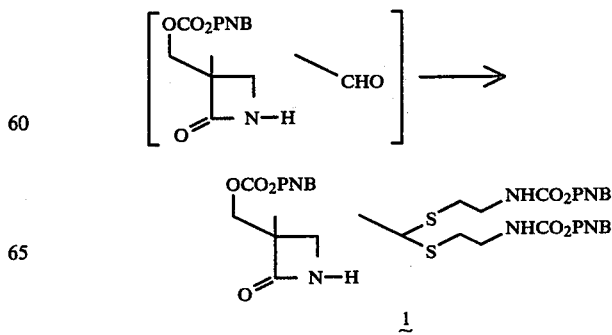

PNB = 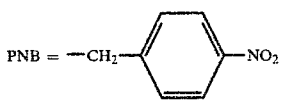

To 6.75 ml anhydrous pyridine (mw=79; ρ=0.982; 83.9 mmole) in 350 ml anhydrous acetonitrile is added 4.05 g anhydrous powdered chromium trioxide (mw=100; 40.5 mmole). After stirring at room temperature (25° C.) for 30 minutes, 9.6 g dried Supercell is added and stirring is continued for 5 additional minutes. A solution of 3.21 g 3-methyl-3-(p-nitrobenzylcarbonyldioxymethyl)-4-(2-hydroxyethyl)-2-azetidinone (mw=338; 9.5 mmole) in 30 ml anhydrous acetonitrile is added all at once. The reaction mixture is stirred under anhydrous conditions at room temperature (25° C.) for one hour. Addition of 9.6 g NaHSO₃ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate ~600 ml). The filtrate is concentrated under a N₂ stream to 130 ml total volume. To this solution containing crude aldehyde at 0° C. under N₂ is added 9.64 g p-nitrobenzyloxycarbonylaminoethanethiol (mw=256; 37.7 mmole) as prepared below (Example 12, Step B). To the stirred reaction mixture is added 8.0 ml boron trifluoride etherate (mw=142; ρ=1.125; 63.4 mmole). After 1.5 hours at 0° C., the reaction mixture is poured into a stirred ice-cold mixture of 69 g K₂HPO₄-500 ml H₂O and 700 ml ethyl acetate (EA). The layers are separated, and the aqueous one is saturated with NaCl and re-extracted with additional EA. The combined organic layers are washed twice with brine, dried over anhydrous MgSO₄ and filtered. The filtrate is concentrated under a N₂ stream and then pumped on high vacuum to give crude 1.

The material is chromatographed on 450 g silica gel (column height=48 cm; diameter=5.5 cm) packed and applied in CHCl₃ and eluted with increasing percentages of MeOH in CHCl₃ (0–4% MeOH/CHCl₃). Those fractions containing the desired product are combined, concentrated under a N₂ stream; and pumped on high vacuum to give 1.

Step B
Preparation of p-Nitrobenzyloxycarbonylaminoethanethiol

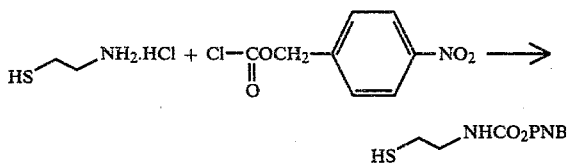

To 600 ml diethyl ether (Et₂O)-75 ml H₂O in an ice bath with stirring is added 3.2 g cysteamine hydrochloride 8mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g p-nitrobenzyloxycarbonylaminoethanethiol (65% yield).

NMR (CDCl₃) 8.18 (d, J=8 Hz, aromatic protons ortho to nitro), 7.47 (d, J=8 Hz, aromatic protons meta to nitro), 5.27 (—NH—), 5.20 (s, —CH₂— φ-pNO₂), 3.40 (m, —CH₂—NH—), 2.67 (m, —CH₂—SH), 1.35 (t, J=8.5 Hz, —SH) in ppm downfield from TMS.

IR (CHCl₃ solution) carbonyl-~1725 cm⁻¹.

M.S.-molecular ion-256, (M-47) at 209, (M-136) at 120, ⁺CH₂φpNO₂ at 136.

Step C

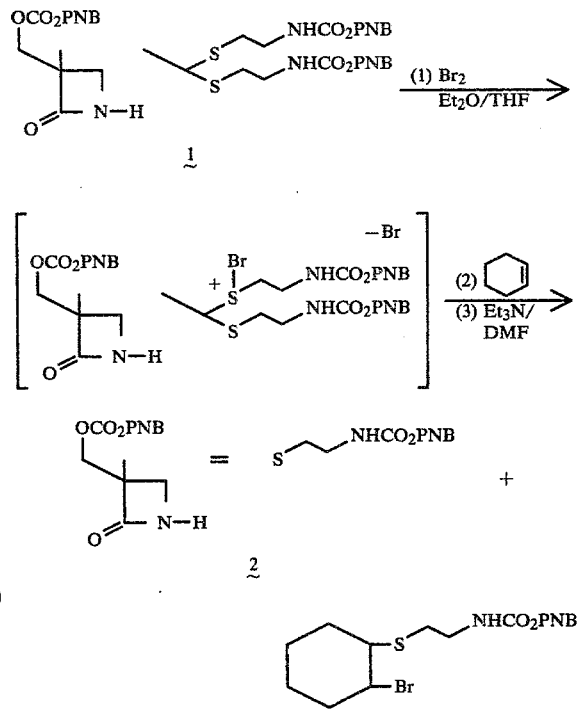

To 14.2 pentane (dried over 4 A Linde molecular sieves) is added 0.5 ml Br₂ (mw=160; 9.75 mmole). To 5 g of 1 (mw=830; 6.02 mmole) in 58 ml tetrahydrofuran (THF) (freshly distilled from lithium aluminum hydride) (LAH) and 65 ml Et₂O (dried over 3 A 1/16" Linde molecular sieves) at 0° C. under N₂ with stirring is added dropwise 10 ml of the above 0.66 M Br₂ solution (6.6 mmole). After 10 minutes at 0° C., 0.67 ml cyclohexene (mw=82; ρ=0.81; 6.6 mmole) is added. After 5 minutes at 0° C., 1.7 ml triethylamine (mw=101; ρ=0.729; 12.3 mmole) is added immediately followed by 40 ml ice-cold dimethylformamide (DMF) (distilled from anhydrous CaSO₄ at 40 mm and stored over 4 A Linde molecular sieves). The ice bath is removed, and stirring is continued for 2¼ hours at room temperature. The reaction mixture is poured into a stirred ice-cold mixture of 12.6 ml 1 MKH₂PO₄ 160 ml H₂O-500 ml (EA). After separation of the layers, the aqueous one is saturated with sodium chloride and re-extracted with EA. The combined organic layers are extracted once with brine, dried over anhydrous MgSO₄, filtered and concentrated under a N₂ stream followed by pumping under high vacuum to provide crude 2.

The material is chromatographed on 250 g silica gel (height=45 cm; diameter=4.5 cm) packed and applied in CHCl₃ and eluted with increasing percentages of MeOH in CHCl₃ (0–3% MeOH/CHCl₃). Those fractions containing clean product are combined, concentrated under a N₂ stream, and pumped on high vacuum to give 2. Contaminated fractions are rechromatographed on silica gel using increasing percentages of EA in CHCl₃ (0–25% EA/CHCl₃) to give additional 2.

STEP D

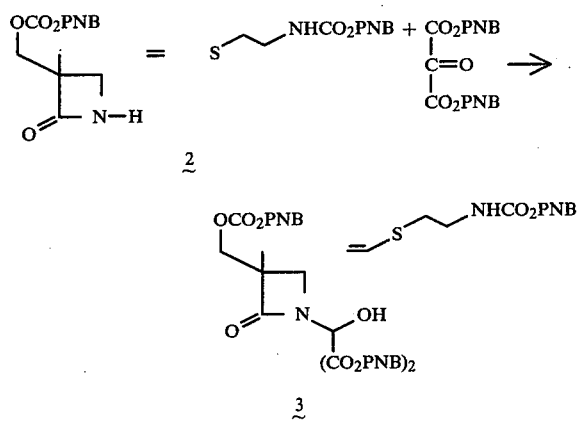

To a stirred solution of 2.48 g di(p-nitrobenzyl) ketomalonate (from Example 12, Step E) (mw=388; 6.39 mmole) in 400 ml hot anhydrous toluene is added a solution of 2.52 g of 2 (mw=574; 4.39 mmole) in 20 ml THF (distilled from LAH) and 40 ml anhydrous toluene. After some of the solvent is boiled off, additional anhydrous toluene is added, and the azeodrying process is repeated three times. The solution is then refluxed under N₂ for 30 minutes. Additional toluene is then allowed to boil off yet the volume is not allowed to diminish so much that precipitation occurs. Total heating time is approximately 2½ hours. The clear yellow reaction mixture is removed from the oil bath and placed under a stream of N₂ which instantaneously causes clouding. After concentration to a yellow oil, the residue is dissolved in CH₂Cl₂, dried over anhydrous MgSO₄, filtered, and concentrated under a N₂ stream to give crude 3.

The material is chromatographed on 250 g silica gel packed and applied in CHCl₃ (height=43 cm; diameter=4.5 cm). Elution with 500 ml 0.5% MeOH/CHCl₃ is followed by continued elution with 1% MeOH/CHCl₃ for the remainder of the chromatography. After the emergence of excess reagent, those fractions containing pure 3 are combined, concentrated under a N₂ stream and then on high vacuum to give 3.

Later fractions containing 3 and the corresponding cis thioenol ether are re-chromatographed on silica gel to give additional 3.

Step E
Preparation of di-p-Nitrobenzyl Ketomalonate

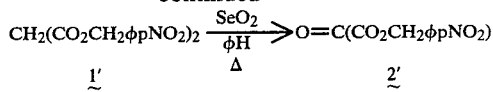

φH = benzene

A mixture of 100 g p-nitrobenzyl bromide (0.46 mole), 28.6 g malonic acid (0.275 mole) and 750 ml ethanol (EtOH) is stirred and warmed on the steam bath until solution is achieved. A solution of 33 g KOH (>85% purity; ~0.6 mole) in 200 ml of water is added carefully with swirling. An additional 200 ml of water is added, and the two-phase system is refluxed for 1.8 hours. The lighter color homogeneous solution is cooled in ice for 1 hour and the crude product isolated by filtration, washed twice with a minimum of cold EtOH, and dried by pulling dry N₂ through the cake; 33.7 g of solid is obtained. If, during the refluxing stage the reaction mixture is slowly concentrating to ca. half volume by allowing refluxing solvent to distill off, the crude product yield rises to 77 g. The material is recrystallized from methanol to give pure di-p-nitrobenzyl malonate 1'.

A mixture of 23.4 of 1', 10 g SeO₂, and 30–40 ml of xylene is stirred in a flask immersed in an oil bath. The bath temperature is raised over 1 hour to 130°–135°. A gradual darkening of the reaction mixture is noted, and after a total of 4 hours at 130°–135°, most of the insoluble residue is black Se°. The mixture is cooled, MgSO₄ is added to remove the water, and Celite is added to aid in filtration. The mixture is filered through Celite and the cake washed with xylene and a small portion of EtOAc. Final volume: 60 ml. A 100 g column of Baker Silica Gel is prepared in benzene and 10 ml of filtrate applied, then eluted with increasing amounts of EtOAc in benzene, 500 ml fractions being collected. After one 2% ethyl acetate (EtOAc)/φH, and two 10% EtOAc/φH fractions, the third 10% and first 20% EtOAc/φH provide the bulk of the product (~1.6 g from 10 ml filtrate) as judged by tlc (20% EtOAc/CHCl₃; silica gel GF). Recrystallization from benzene, (1 g in ca. 50 ml concentrated to ~⅝ volume and "spiked" with 1 ml of H₂O saturated benzene): provides 0.24 g 2'; mp (117) 121°–122°.

Step F

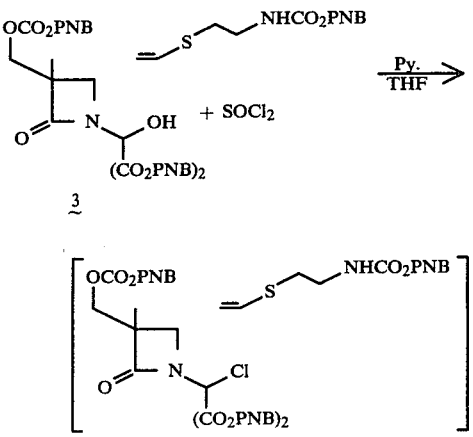

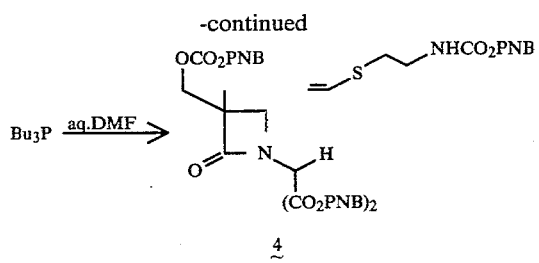

A solution of 1.46 g of 3 (mw=962; 1.53 mmole) in $CH_2Cl_2$ is dried over anhydrous $MgSO_4$, filtered, concentrated under a $N_2$ stream, and dried further under high vacuum just prior to the following reaction. To a solution of 3 in 24 ml THF (freshly distilled from LAH) at −20° C. is added 0.206 ml anhydrous pyridine (mw=79; ρ=0.982; 2.56 mmole). With stirring under $N_2$, 294 mg of freshly distilled thionyl chloride (mw=119; 2.47 mmole) in 5 ml THF is added dropwise. The reaction mixture is stirred for 10 minutes at −20° C., then ½ hour at 0° C. and finally 1 hour at 25° C. The pyridine hydrochloride is filtered under $N_2$ and washed with 20 ml THF. The filtrate is concentrated under $N_2$ stream followed by pumping on high vacuum. The resulting yellow foam is swirled in 25 ml anhydrous THF, and a small amount of orange-red insoluble material is filtered off under $N_2$. The filtrate is reconstituted as above to a yellow foam.

To this freshly prepared chloro compound is added with stirring a freshly shaken suspension of 678 mg tributylphosphine (mw=202; 3.36 mmole) in 36.5 ml 9:1 DMF-$H_2O$ followed by 294 mg $K_2HPO_4$ (mw=174; 1.69 mmole). The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous $MgSO_4$, filtered and concentrated under a $N_2$ stream followed by pumping on high vacuum to give crude 4.

The material is chromatographed on 100 g silica gel (height=28.5 cm; d=4 cm) packed and applied in $CHCl_3$ and eluted with 0.5% MeOH in $CHCl_3$. Those fractions containing clean product are combined, concentrated under a $N_2$ stream and then on high vacuum to give 4. Contaminated fractions are re-chromatographed on silica gel thin layer plates (eluant=50% acetone/hexane; extraction of desired u.v. band with $CHCl_3$ and EA to provide additional 4.

Step G

To 8.5 ml pentane (dried over 4 A Linde molecular sieves) is added 0.2 ml $Br_2$ (mw=160; 3.9 mmole). To 0.706 g of 4 (mw=946; 0.746 mmole) in 18 ml THF (freshly distilled from LAH) and 5.7 ml $Et_2O$ (dried over 3 A 1/16" Linde molecular sieves) at 0° C. under $N_2$ with stirring is added dropwise 1.8 ml of the above 0.45 M $Br_2$ solution (0.81 mmole). After 15 minutes at 0° C., 0.42 ml triethyl amine (mw=101; ρ=0.729; 3.03 mmole) is added immediately followed by 10.5 ml ice-cold DMF (distilled from $CaSO_4$ at 40 mm and stored over 4 A Linde molecular sieves). The ice-bath is removed, and stirring at room temperature is continued for 2 hours. The reaction mixture is poured into a stirred ice-cold mixture of 3.1 ml 1 M $KH_2PO_4$-70 ml $H_2O$-100 ml EA. The layers are separated, and the aqueous one is saturated with NaCl and re-extracted with EA. The combined organic layers are washed once with brine, dried over anhydrous $MgSO_4$, and filtered. The filtrate is concentrated under a $N_2$ stream and then pumped on high vacuum to give crude 5.

The material is chromatographed on 60 g silica gel (diameter=2.8 cm) packed and applied in $CHCl_3$ and is eluted with 100 ml-2% $EA/CHCl_3$; 100 ml-4% $Ea/CHCl_3$ and then 5% $EA/CHCl_3$ for the remainder of the chromatography. The fractions containing pure 5 are combined, concentrated under a $N_2$ stream, and pumped on high vacuum to give 5.

Step H

-continued

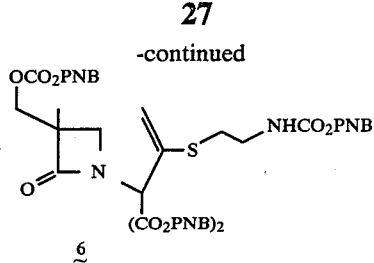

To 29 mg anhydrous silver fluoride (mw=127; 0.23 mmole) is added a solution of 146 mg of 5 (mw=1024; 0.14 mmole) in 3.5 ml anhydrous pyridine. The stoppered reaction mixture is stirred at room temperature in the dark for one hour and then poured into 20 ml cold water-30 ml EA. After separation of the layers, the aqueous one is extracted two times with EA and one time with $CHCl_3$. Each organic layer is extracted one time with $H_2O$ and one time with brine. The combined organic layers are dried over anhydrous $MgSO_4$, filtered, and concentrated under a $N_2$ stream followed by pumping on high vacuum to give crude 6.

Preparative thin layer chromatography (eluant=40% acetone/hexane; repeated extraction of desired u.v. band with a large volume of $CHCl_3$) yields slightly contaminated 6. Re-chromatographing on silica using EA in $CHCl_3$ as an eluting system gives 6.

Step I

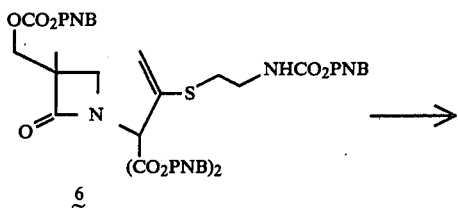

A solution of 77 mg of 6 (mw=944; 0.082 mmole) in 0.9 ml S-coilidine (distilled from powdered KOH~30 mm pressure) is added to 13.4 mg anhydrous LiI (dried for few hours at 100° C. over $P_2O_5$ under vacuum) (mw=134; 0.1 mmole). With stirring under $N_2$, the reaction mixture is heated in an oil bath at 120° C. After a total of 30 minutes, the reaction mixture is cooled to 25° C., diluted with $CH_2Cl_2$, and transferred to a round bottom flask for concentration under a $N_2$ stream and then on high vacuum. Partitioning the residue between EA-$H_2O$ and 1 ml 1 M $KH_2PO_4$ is followed by extraction of the aqueous layer two additional times with EA and one time with $CHCl_3$. Each organic layer is then backwashed with brine. The combined organic layers are dried over anhydrous $MgSO_4$, filtered, concentrated under a $N_2$ stream and then on high vacuum to give crude 7.

Preparative thin layer chromatography on silica gel (plate is eluted two times with 40% acetone/hexane; repeated extraction of the appropriate u.v. bands with large volume of $CHCl_3$) yields recovered starting material and 7.

Step J

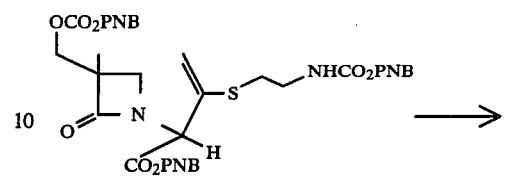

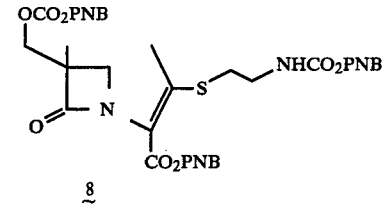

To 49 mg of 7 (mw=765; 0.064 mmole) in 0.7 ml DMSO (distilled from $CaH_2$ at 8 mm and stored over 4A Linde molecular sieves) is added 100 μl diisopropylamine (distilled from NaH under $N_2$ and stored over 4A Linde molecular sieves) (mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a column of silica gel (packed, applied, and eluted with EA) to remove residual DMSO. After concentration under a $N_2$ stream of all fractions having u.v. absorbance, the material is chromatographed on a thin layer silica gel plate (eluant=50% EA/$CHCl_3$; repeated extraction of desired u.v. bands with a large volume of chloroform). Recovered starting material is re-submitted to the reaction conditions and isolation procedure two more times to yield additional 8.

Step K

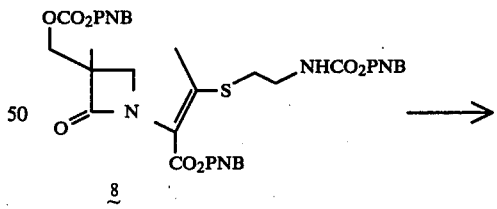

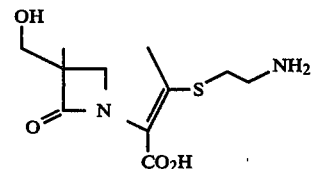

To 5.2 mg 8 is added 0.60 ml dioxane, 0.05 ml ethanol, 0.35 ml deionized water and 0.01 ml of 1.0 M $K_2HPO_4$. To the resultant clear solution is added 5 mg of 10% Pd/C. Th suspension is flushed with $N_2$, then 5-6 times alternately with 50 psi $H_2$ and vacuum. Finally, it is shaken under a 50 psi H₂ atmosphere for 30-40 min. After centrifugation, the Pd/C is washed and centrifuged 2-3X with 0.5 ml portions of deionized water. The combined centrifugates are extracted 5×1-2 ml ether. Residual ether is removed under vacuum and the aqueous solution applied to an XAD-2 column (20×140 mm). Fractions of 100 drops (6-7 ml) are collected, with continuous UV monitoring, by elution with deionized water. Emergence of strongly UV absorbing material begins around fractions 3-5 and is usually complete by fractions 25-30. Early fractions are examined by UV to exclude those few deemed too strongly absorbing in the 270-280 mμ region. The remaining fractions are combined and lyophilized. The residue is evaluated by dissolving in 10.0 ml of deionized water and measuring the UV absorption at 298 mμ indicating a 10-30% yield of desired product.

The following Example specifically illustrates a preferred stereo-selective process embodiment of the present invention. As described above in detail, the starting material is a pure optical isomer of 4-vinyl-2-azetidinone (23, above).

EXAMPLE 13

Step A

Preparation of [1-(t-butyldimethylsilyl)-4-vinyl-2-azetidinone]

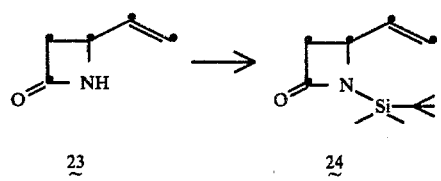

A solution of 23 [4-vinyl-2-azetidinone] (1.153 g, 11.89 mmoles) and triethylamine (1.82 ml, 13.08 mmoles) in anhydrous N,N-dimethylformamide is placed under a nitrogen atmosphere, cooled to 0° C. and treated with t-butyldimethylchlorosilane (1.885 g., 12.48 mmoles) resulting in the immediate appearance of a heavy white precipitate. This mixture is stirred for one hour while gradually warming to room temperature. The mixture is partitioned between 30 ml methylene chloride and 90 ml cold 1 M potassium dihydrogen phosphate. The aqueous phase is extracted with 20 ml methylene chloride. The combined organic phases are washed four times with 30 ml portions of water and finally with 50 ml brine. The methylene chloride solution is dried over anhydrous magnesium sulfate and filtered. The filtrate is evaporated under reduced pressure to give 2.25 g of 24 [1-(t-butyldimethylsilyl)-4-vinyl-2-azetidinone] as a colorless liquid.

NMR (CDCl₃) δ: 6.23-5.10, m, CH=CH₂, 4.07, 7-line m, J=8,6 and 3 Hz, C-4H, 3.35, dd, J=15 and 6 Hz, C-3H cis to C-4H, 2.73, dd, J=15 and 3 Hz, C-3H trans to C-4H, 0.98, s, (CH₃)₃ C Si, 0.23, s, (CH₃)₂ Si, 0.18, s.

Following the above procedure, but making the indicated substitution, the other isomer is obtained.

Step A'

Preparation of 3-methyl-(t-butyldimethylsilyl)-4-vinyl-2-azetidinone

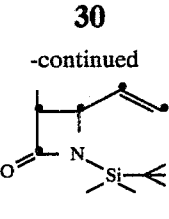

Following the procedure of the preparation of 8-oxo-2,2,7-trimethyl-3-oxa-1-azabicyclo[4.2.0]octane (Example 4b, above), except that an equivalent amount of 1-(t-butyldimethylsilyl)-4-vinyl-2-azetidinone is substituted for the 8-oxo-2,2-dimethyl-3-oxa-1-azabicyclo[4.2.0] octane of Example 4b, the title compound is obtained.

Step B

Preparation of 3-methyl-[1-(t-butyldimethylsilyl)-3-(hydroxymethyl)-4-vinyl-2-azetidinone]

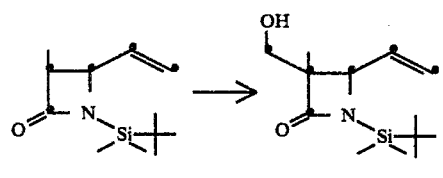

To a solution of freshly prepared lithium diisopropylamide (7.82 mmoles) in 36 ml anhydrous tetrahydrofuran under a nitrogen atmosphere at −75° C. is added a solution of 3-methyl-[1-(t-butyldimethylsilyl)-4-vinyl-2-azetidinone], 24, (1.60 g, 7.11 mmoles) in 10 ml anhydrous THF. The resulting yellow solution of the lithium enolate is, after 16 minutes, treated with excess formaldehyde (see Example 15, below). In 10 minutes, the reaction is quenched by adding 30 ml of a saturated aqueous ammonium chloride solution. This mixture is extracted with 50 ml and 25 ml portions of ethyl acetate. The combined ethyl acetate solutions are washed with 50 ml of brine and dried over anhydrous magnesium sulfate. The drying agent is removed by filtrate is evaporated in vacuo to give the crude product as a yellow oil. Purification by chromatography on silica gel eluting with 10% ethyl acetate/chloroform gives 3-methyl-[1-(t-butyldimethylsilyl)-3-(hydroxymethyl)-4-vinyl-2-azetidinone], 25.

Step C

Preparation of 3-methyl-1-(t-butyldimethylsilyl)-3-(1-p-nitrobenzylcarbonyldioxymethyl)-4-vinyl-2-azetidinone

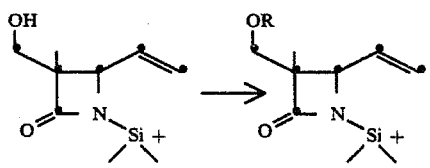

-continued

Step C
Preparation of 3-methyl-1-(t-butyldimethylsilyl)-3-(1-p-nitrobenzylcarbonyldioxymethyl)-4-vinyl-2-azetidinone

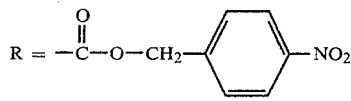

Under nitrogen at −78° C. a solution of 25 (56 mg, 0.220 mmole) in 1 ml of anhydrous tetrahydrofuran is treated with 2.4 M n-butyllithium in hexane (101 μl, 0.242 mmole). To this solution is added, in five minutes, a solution of p-nitrobenzyl chloroformate (52 mg, 0.242 mmole) in anhydrous tetrahydrofuran. After stirring at −78° C. for a period of 55 minutes, 10 ml of a saturated aqueous ammonium chloride solution is added and the product extracted into ethyl acetate. The combined ethyl acetate solutions are washed with brine and dried over anhydrous magnesium sulfate. The drying agent is removed by filtration, and the filtrate is evaporated in vacuo to give crude 26. Purification by preparative thicklayer chromatography on silica gel developing with 5% ethyl acetate/chloroform gives 26.

Step D
Desilylation of 26 to provide 27 [3-methyl-3-(p-nitrobenzylcarbonyldioxymethyl)-4-vinyl-2-azetidinone]

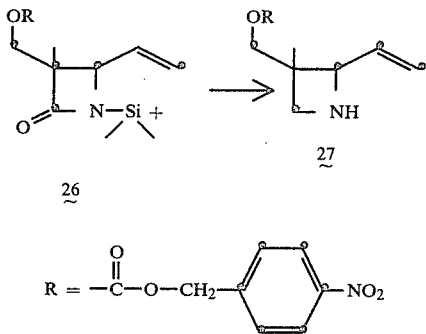

A solution of 26 [1-(t-butyldimethylsilyl)-3-methyl-3-p-nitrobenzylcarbonyldioxymethyl)-4-vinyl-2-azetidinone] (61 mg, 0.141 mmole) in 2 ml of 0.5 N HCl/MeOH is stirred at room temperature (25° C.) for a period of 3 hours. The solution is then cooled to 0° C. and neutralized by the addition of 5 ml of 5% aqueous sodium bicarbonate. The product is extracted into ethyl acetate (10 ml, 2×5 ml). The combined ethyl acetate solutions are washed with water (2×5 ml) and 10 ml brine and then dried over anhydrous magnesium sulfate. The drying agent is removed by filtration, and the filtrate is evaporated in vacuo to give an oil. Preparative thick-layer chromatography of this material on silica gel developing with 10% ethyl acetate/chloroform gives 3-methyl-3-(p-nitrobenzylcarbonyldioxymethyl)-4-vinyl-2-azetidinone, 27.

Step E
Preparation of 14 via 28 by sulfenyl halide addition and dehydrohalogenation

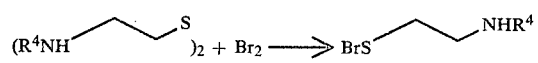

Step E
Preparation of 14 via 28 by sulfenyl halide addition and dehydrohalogenation

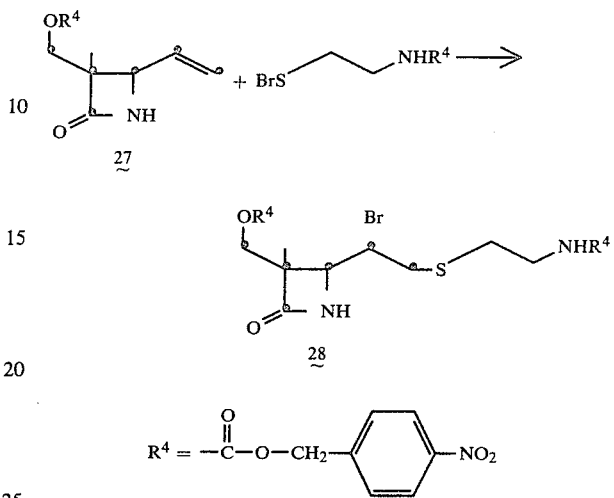

A solution of N-p-nitro CBZ cysteamine disulfide, 96 mg (0.19 mmoles) in 1.5 ml THF (freshly distilled from LiAlH₄) is cooled to −25° C. and treated dropwise with stirring with 0.5 ml of a solution of 135 mg Br₂ in sieve dried CCl₄ (2.2 ml final volume; portion added is equivalent to 0.19 mmoles of Br₂). The resultant orange solution is stirred at −20° C. for 5 min. then treated with 54.0 mg of the vinyl azetidinone, 27, in 0.5 ml sieve dried CH₂Cl₂. The color lightens to yellow. The mixture is allowed to come to 0° C. over 5–10 minutes. Examination by tlc (silica 5% MeOH in CH₂Cl₂ or 20% EtOAc in CH₂Cl₂) shows a main spot with R$_f$ and Ce$^{IV}$+/H+/heat characteristics different from either disulfide or starting 4-vinyl-2-azetidinone. The reaction mixture is concentrated to 0.5 ml under N₂, streaked directly on two 8″×8″ 1000μ silica GF plates, and developed with 20% EtOAc in CH₂Cl₂. The main band under U.V., is scraped off, and extracted with EtOAc to give 28.

Step F

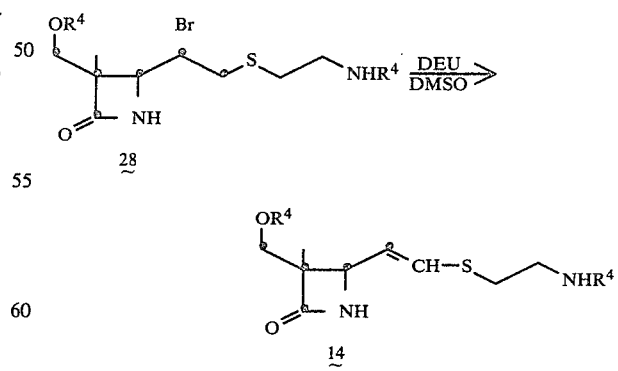

The bromosulfide, 28, 77.0 mg (0.162 mmole) is dissolved in 1.0 ml sieve stored DMSO (distilled from CaH₂), and stirred under nitrogen while 25 λDBU (0.19 mmole) is added. After 3 hours, the mixture is poured into water/KH₂PO₄ and extracted repeatedly with EtOAc. The combined extracts are washed twice with water, dried with anhydrous MgSO₄ and evaporated under nitrogen. The crude product, is streaked on an 8×8″ 1000μ silica GF plate and developed with 20% EtOAc in CH₂Cl₂ to give 14.

EXAMPLE 14

Preparation of Bis (p-Nitrobenzyloxycarbonylaminoethyl)disulfide

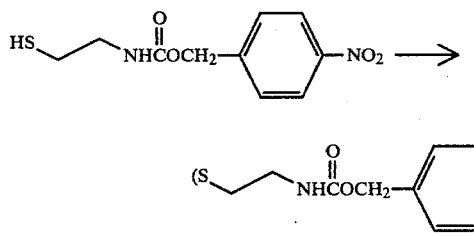

Under nitrogen at −20° C., bromine (1.21 ml, 0.022 mmole) is added to a solution of p-nitrobenzyloxycarbonylaminoethanethiol (11.28 g, 0.044 mole) in 100 ml of anhydrous tetrahydrofuran. The cooling bath is removed, and the cold solution is stirred for 15 minutes. The solution is then diluted with 400 ml ethyl acetate and washed with 200 ml 1 M pH 7 phosphate buffer, 200 ml 1 M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis (p-nitrobenzyloxycarbonylaminoethyl)disulfide:

| | |
|---|---|
| IR (CH₂Cl₂) μ: | 3.04NH |
| | 5.96 carbonyl |
| | 6.22, 6.61 nitro |
| NMR (CDCl₃)δ: | 8.24 ⎫ |
| | ⎬ d, J = 8.5Hz, ArH |
| | 7.54 ⎭ |
| | 5.37, broad s, NH |
| | 5.26, s, ArCH₂O |
| | 3.60, q, J = 6Hz and 6Hz, NHCH₂CH₂ |
| | 2.86, t, J = 6Hz, NHCH₂CH₂S |

EXAMPLE 15

Preparation of 8-oxo-2,2-dimethyl-7α and β-hydroxymethyl-3-oxa-1-azabicyclo[4.2.0]octane

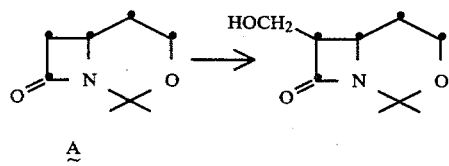

The procedure of Example 5, substituting A for 8-oxo-2,2,7-trimethyl-3-oxa-1-azabicyclo[4.2.0]octane, is carried out. Upon purification by silica gel chromatography, the title compound is obtained.

EXAMPLE 16

Preparation of 3-(2-aminoethylthio)-6-hydroxymethyl-7-oxo-1-azabicyclo[3.2.0]hept-2-ene-2-carboxylic acid

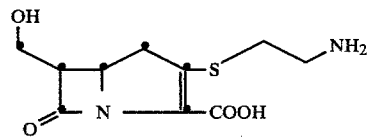

Following the procedure described above for the preparation of 6-methyl-6-hydroxymethyl-7-oxo-1-azabicyclo [3.2.0]hept-2-ene-2-carboxylic acid, except that in Example 6 an equivalent amount of 8-oxo-2,2-dimethyl-7-hydroxymethyl-3-oxa-1-azabicyclo[4.2.0]octane rather than the 2,2,7-trimethyl species is taken; the title compound is obtained when the procedures of Examples 6,7 and 12 are followed.

EXAMPLE 17

Preparation of 8-oxo-2,2-dimethyl-7α and β-(1-hydroxy-2-phenylethyl)-3-oxa-1-azabicyclo[4.2.0]octane

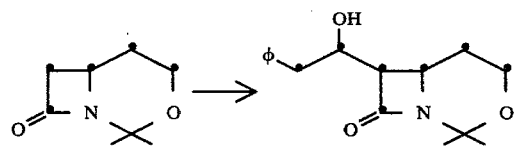

Following the procedure of Example 15, except that instead of formaldehyde, an equivalent amount of phenylacetaldehyde is used, upon purification by silica gel chromatography, the title compound is obtained.

EXAMPLE 18

Preparation of 3-(2-aminoethylthio)-6-(1-hydroxy-2-phenylethyl)-7-oxo-1-azabicyclo[3.2.0]hept-2-ene-2-carboxylic acid

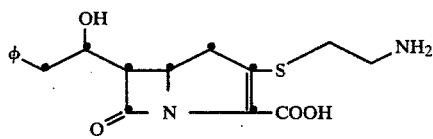

Following the procedure of Example 16 except that 8-oxo-2,2-dimethyl-7(1-hydroxy-2-phenylethyl)-3-oxa-1-azabicyclo[4.2.0]octane is substituted in equivalent amount for its analogous substrate, the title compound is obtained.

EXAMPLE 19

Preparation of 8-oxo-2,2-dimethyl-7α-benzyl-3-oxa-1-azabicyclo [4.2.0]octane

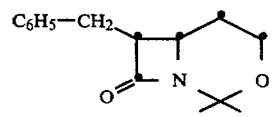

Following the procedure described for the preparation of 8-oxo-3-oxa-2,2-dimethyl-7α-isopropyl-1-azabicyclo [4.2.0]-octane from 8-oxo-3-oxa-2,2-dimethyl-1-azabicyclo[4.2.0]-octane (Example 4a, above) and using benzyl bromide instead of isopropyl iodide there is obtained 8-oxo-2,2-dimethyl-7α-benzyl-3-oxa-1-azabicyclo[4.2.0]octane.

i.r. μ: 5.73 (β-lactam).

n.m.r. δ: 1.33S, 1.75S (gem dimethyl); 1.74 m (C-5 H) 3.0 d of d (C₆H₅—CH₂); 3.73 d of d (C-2 H) 7.25S (C₆H₅).

EXAMPLE 20

Preparation of 8-oxo-2,2-dimethyl-7α and β-benzyl-7β and α-(1-hydroxyethyl)-3-oxa-1-azabicyclo[4.2.0]octane

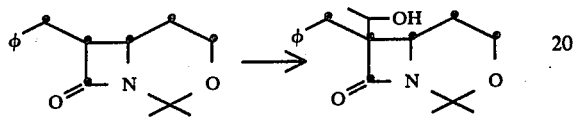

Using the procedure of Example 5 but substituting an equivalent amount of 8-oxo-2,2-dimethyl-7α-benzyl-3-oxa-1-azabicyclo[4.2.0]octane (Example 19) for 8-oxo-2,2,7-trimethyl-3-oxa-1-azabicyclo[4.2.0], and an equivalent amount of acetaldehyde for formaldehyde, there is obtained, upon purification by silica gel chromatography, the title compounds.

EXAMPLE 21

Preparation of 8-oxo2,2-dimethyl-7α(1-mesyloxyethyl)-3-oxa-1-azabicyclo[4.2.0]octane

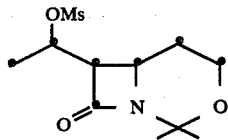

Under nitrogen at 0° a solution of rel-(6S,R)-8-oxo-2,2-dimethyl-7,1R-hydroxyethyl-3-oxa-1-azabicyclo[4.2.0]octane and rel(6S,7R) 8-oxo-2,2-dimethyl-7,1S-hydroxyethyl-3-oxa-1-azabicyclo-[4.2.0]octane as an approximately 1:2 diastereomeric mixture (128 mg, 0.643 mm) and triethylamine (134 μl or 0.965 mm) in 5 ml of sieve dried methylene chloride is treated with redistilled methane sulfonyl chloride (55 μl or 0.707 mm). The resulting solution is stirred for 30 minutes. It is then washed with 10 ml each of cold water, 1 molar pH 3 phosphate buffer, 5% sodium bicarbonate, water and finally brine. The organic phase is dried over magnesium sulfate and filtered. The filtrate is evaporated in vacuo to give 156 mg of a pale yellow oil. This material is chromatographed on preparative thick layer silica gel plates developed four times with 1:9 acetone/hexane to give a separated diastereomeric mesylate in 68% overall yield.

Diastereomer of R$_f$.13 (25%) -
i.r. CH₂Cl₂ μ, 5.73 β-lactam.
n.m.r. C₆D₆ δ 5.06–4.61, 8 line multiplet, 1H, J = 6.5 and 7.5 Hz, CH₃CH
3.58–3.26 multiplet 3H, C₄—methylene, C₆—methine
2.61, dd, 1H, J = 1.8 and 7.5 Hz, C₇—methine.

2.40, s, 3H, CH₃SO₂
1.83, s, 3H ⎫
1.09, s, 3H ⎬ C—2 methyls
1.30, d, 3H, J = 6.5 Hz, CH₃CH
Diastereomer of R$_f$.08 (43%)
i.r. CH₂Cl₂ μ β-lactam 5.71
n.m.r. C₆D₆ δ 5.04–4.64, 8 line multiplet 1H, J = 4.5 and 6.5 Hz, CH₃CH
3.63–3.10 multiplet, 3H, C₄—methylene and C₆ methine.
2.67 dd, 1H, J = 1.8 and 4.5 Hz, C₇—methine
2.46, s, 3H, CH₃SO₂
1.81, s, 3H ⎫
1.16, s, 3H ⎬ C—2 methyls
1.34, d, 3H, J = 6.5 Hz, CH₃CH.

EXAMPLE 21a

Preparation of 8-oxo-2,2-dimethyl-7α-(1-azidoethyl)-3-oxa-1-azabicyclo[4.2.0]octane

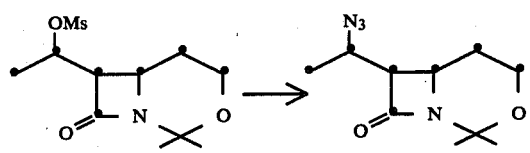

A solution of lithium azide, prepared by stirring over night a mixture of 170 mg sodium azide and 100 mg lithium chloride in 3 ml of anhydrous dimethyl sulfoxide, followed by filtration, is added to 160 mg of 8-oxo-2,2-dimethyl-7α(1-mesyloxyethyl)-3-oxa-1-azabicyclo-[4.2.0]octane and stirred under nitrogen at 25° C. for eight hours or until the reaction is judged complete by tlc. The mixture is then poured into 10 ml ice water and extracted with ethyl acetate, the combined extracts washed once with water, once with saturated sodium chloride solution, dried (MgSO₄) and evaporated under a nitrogen stream. The crude product is purified by preparative tlc to afford the title compound.

EXAMPLE 22

Preparation of 8-oxo-2,2-dimethyl-7α-(1-p-nitrobenzyloxycarbonylaminoethyl)-3-oxa-1-azabicyclo[4.2.0]octane

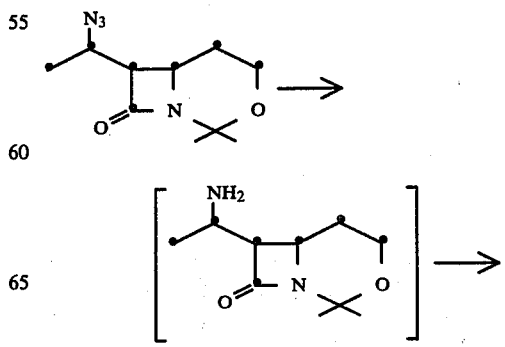

-continued

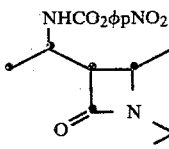

A mixture of 107 mg of 8-oxo-2,2-dimethyl-7α-(1-azidoethyl)-3-oxa-1-azabicyclo[4.2.0]octane and 50 mg of 10% Pd/C in 2 ml of anhydrous dioxane is shaken under 3 atmospheres of hydrogen for 1.5 hours. The mixture is filtered and concentrated to 1 ml under a nitrogen stream, then treated with 1 ml of 1 M K₂HPO₄ and 1 ml methylene chloride. The mixture is stirred vigorously in an ice bath under nitrogen while a solution of 120 mg of p-nitrobenzylchloroformate in 0.5 ml methylene chloride is added dropwise over one minute. The solution is stirred for another 15 minutes, then treated with 0.1 ml pyridine in 2 ml water and stirred vigorously for another 15 minutes. The organic phase is removed and the aqueous phase is extracted several more times with methylene chloride. The combined organic phases are washed twice with water, once with saturated NaCl, dried (MgSO₄) and evaporated under reduced pressure. Purification by preparative tlc affords the title compound.

EXAMPLE 23

Preparation of 8-oxo-2,2-dimethyl-7[(1-o-nitrobenzylthioethyl)-3-oxa-1-azabicyclo[4.2.0]octane

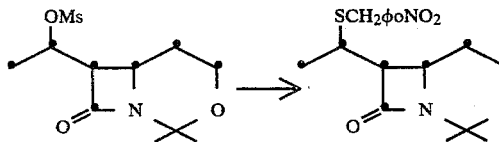

When in Example 21a an equivalent solution of o-nitrobenzyl mercaptan in DMF is substituted for the lithium azide solution, the title compound is obtained.

EXAMPLE 24

Preparation of 4(2,2-bisbenzylthioethyl)-3-methyl-3 (p-nitrobenzylcarbonyldioxymethyl)-2-acetidinone

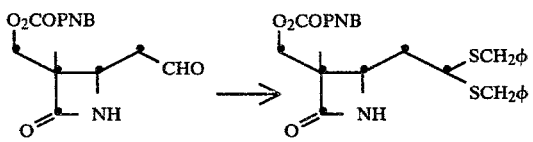

When in Example 12, Step A, an equivalent amount of benzyl mercaptan is substituted for 2-(p-nitrobenzyloxycarbonylamino)ethane thiol, the title compound is obtained.

EXAMPLE 25

Preparation of 3-methyl 4-(2,2-bis-o-nitrobenzylthioethyl)-3-(-p-nitrobenzylcarbonyldioxymethyl)-2-azetidinone

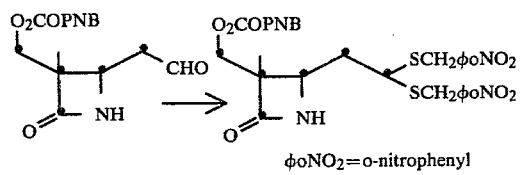

φoNO₂=o-nitrophenyl

When in Example 12, Step A, an equivalent amount of o-nitrobenzylthiol is substituted for 2-(p-nitrobenzyloxycarbonylamino)ethane thiol, the title compound is obtained.

EXAMPLE 26

Preparation of 3-methyl 3-(p-nitrobenzylcarbonyldioxymethyl)-4β-[1-bromo-2-(2-p-nitrobenzyloxycarbonylamino) 1,1-dimethylethylthio)ethyl]-2-azetidinone

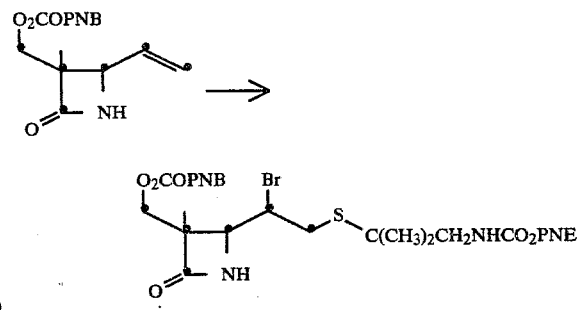

If in Example 13, Step E, an equivalent solution of 2-(p-nitrobenzyloxycarbonylamino)-1,1-dimethylethylsulfenyl bromide, prepared by cleavage of bis(2-(p-nitrobenzyloxycarbonylamino)-1,1-dimethylethylthio)mercury with bromine in THF/ether at 0° C., is substituted for the solution of 2-(p-nitrobenzyloxycarbonylamino)ethylsulfenyl bromide, the title compound is obtained.

EXAMPLE 27

Preparation of 3-benzylthio-6-methyl-6-hydroxymethyl-7-oxo-1-azabicyclo[3.2.0]hept-2-ene-2-carboxylic acid

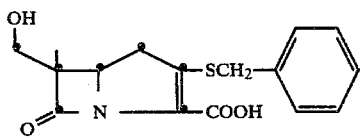

Following the procedure of Example 12, Steps A-K except substituting for the indicated azetidinone the azetidinone of Example 24, the title compound is obtained.

EXAMPLE 28

Preparation of 3-(2-amino-1,1-dimethylethylthio)-6-methyl-6-(1-hydroxymethyl)-7-oxo-1-azabicyclo[3.2.0]hept-2-ene-2-carboxylic acid

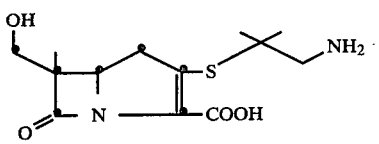

Following the procedure of Example 13, Step F, except substituting for the indicated azetidinone the azetidinone of Example 26, followed by the reactions corresponding to those of Example 12 D-K, the title compound is obtained.

EXAMPLE 29

Preparation of 3-mercapto-6-methyl-6-(p-nitrobenzylcarbonyldioxymethyl)-7-oxo-1-azabicyclo-[3.2.0]hept-2-ene-2-carboxylic acid, p-nitrobenzyl ester

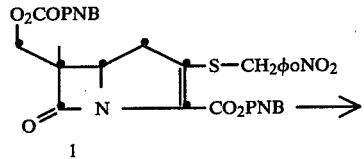

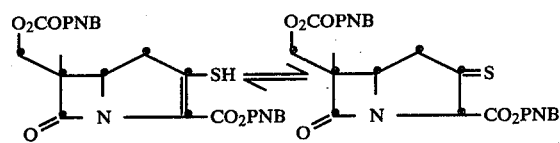

A solution of 5 mg of 1 (prepared from the azetidinones of Example 25 and the procedure of Example 12) in 0.6 ml of dioxane is irradiated for one hour in a pyrex vessel under nitrogen with nitrogen being slowly bubbled through (1 bubble per 5 sec.) using 300 nm sources in a Rayonet apparatus, to give the title compound as a mixture of thiol-thione tautomers.

EXAMPLE 30

Preparation of 6-Methyl-6-(hydroxymethyl)-3-mercapto-7-oxo-1-azabicyclo[3.2.0]hept-2-ene-2-carboxylic acid

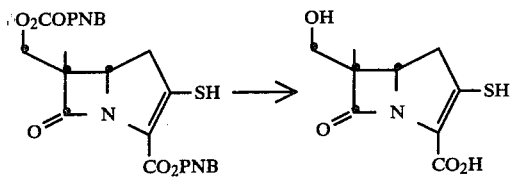

If the solution obtained after irradiation in Example 29 is immediately treated with 0.05 ml of ethanol, 0.35 ml deionized water, 0.01 ml of 1.0 M $K_2HPO_4$, and 5 mg of 10% Pd/C and then treated as in Example 12, Step K, except that instead of purification on the XAD-2 column the ether extracted aqueous solution is cooled in ice, carefully acidified to pH 2 and extracted with ethyl acetate, and the combined extracts then washed once with saturated NaCl solution, dried with $MgSO_4$ and concentrated under a stream of $N_2$, the title compound is obtained.

EXAMPLE 31

Following the procedure of the foregoing Examples and text, the following representative compounds of the present invention (Table I) are obtained by analogy.

TABLE I

| Compound | $R^8$ | $R^6$ | $R^7$ | Remarks |
|---|---|---|---|---|
| (1.) | $-(CH_2)_3NH_2$ | H | $CH_2OH$ | From $BrS(CH_2)_3NHCO_2PNB$, Example 13, Step E; or $HS(CH_2)_3NHCO_2PNB$, Example 12, Step A. |
| (2.) | $-(CH_2)_3NHC(=NH)H$ | H | $CH_2OH$ | From Compound 1. of Example 31 in reaction with methyl formimidate hydrochloride in water at pH 8.5. |
| (3.) | $-(CH_2)_3NHC(=NH)CH_3$ | H | $CH_2OH$ | From Compound 1. of Example 31 in reaction with ethyl acetimidate hydrochloride in water at pH 8.5. |
| (4.) | $-\text{C}_6\text{H}_4-CH_2NH_2$ | H | $CH_2OH$ | From $HS-C_6H_4-CH_2NHCO_2PNB$, Example 12, Step A. |

TABLE I-continued $$\text{structure with } R^6, R^7, SR^8, COOH, \text{ β-lactam ring}$$  I

| Compound | R⁸ | R⁶ | R⁷ | Remarks |
|---|---|---|---|---|
| (5.) | ![phenyl-CH₂NHC(=NH)H] | H | CH₂OH | As in 2., above. |
| (6.) | ![phenyl-CH₂NHC(=NH)CH₃] | H | CH₂OH | As in 3., above. |
| (7.) | ![m-(CH₂NH₂)-phenyl] | H | CH₂OH | From HS—[m-(CH₂NHCO₂PNB)-phenyl], Example 12, Step A. |
| (8.) | ![phenyl-CH₂NHC(=NH)H] | H | CH₂OH | As in 2., above. |
| (9.) | ![phenyl-CH₂NHC(=NH)CH₃] | H | CH₂OH | As in 3., above. |
| (10.) | ![5-methyl-1,3,4-thiadiazol-2-yl] | H | CH₂OH | From HS—[5-methyl-1,3,4-thiadiazol-2-yl], Example 12, Step A. |
| (11.) | —CH(CH₃)—CH₂—NH₂ | H | CH₂OH | From HSCH(CH₃)CH₂NHCO₂PNB, Example 12, Step A; or BrSCH(CH₃)CH₂NHCO₂PNB, Example 13, Step E. |
| (12.) | —CH₃ | H | CH₂OH | From HSCH₃, Example 12, Step A; of BrSCH₃, Example 13, Step E. |
| (13.) | —phenyl | H | CH₂OH | From HSφ, Example 12, Step A; or BrSφ, Example 13, Step E. |
| (14.) | ![1-methyl-1,2,3,4-tetrazol-5-yl] | H | CH₂OH | From: HS—[1-methyl-tetrazol-5-yl], Example 12, Step A. |
| (15.) | —CH₂CH(NH₂)CH₃ | H | CH₂OH | From HSCH₂CH(CH₃)NHCO₂PNB, Example 12, Step A; of BrSCH₂CH(CH₃)NHCO₂PNB, Example 13, Step E. |
| (16.) | —CH₂C(NH₂)(CH₃)CH₃ | H | CH₂OH | From HSCH₂C(CH₃)₂NHCO₂PNB, Example 12, Step A; of BrSCH₂C(CH₃)₂NHCO₂PNB, Example 13, Step E. |
| (17.) | ![4-pyridyl] | | | From SH—[4-pyridyl], Example 12, Step A. |

TABLE I-continued

|  | | | | I |
|---|---|---|---|---|

| Compound | R⁸ | R⁶ | R⁷ | Remarks |
|---|---|---|---|---|
| (18.) | —SCH₂CH₂NH₂ | H | CH₂OH | |
| (19.) | —SCH₂CH₂NH₂ | H | CH₃CH—<br>\|<br>NH₂ | |
| (20.) | —SCH₂CH₂NH₂ | H | CH₃CH—<br>\|<br>Cl | |
| (21.) | —SCH₂CH₂NH₂ | CH₃ | CH₃CH—<br>\|<br>OH | |
| (22.) | —Sφ | CH₃ | CH₃CH—<br>\|<br>NH₂ | |
| (23.) | —SCH₂CH₂CH₂NH₂ | CH₃ | CH₂CH<br>\|<br>OH | |
| (24.) | —Sφ | CH₃ | CH₂OH | |

EXAMPLE 33

Preparation of the N-Formimidoyl derivative of 3-(2-aminoethylthio)-6-methyl-6-(hydroxymethyl)-7-oxo-1-azabicyclo[3.2.0]hept-2-ene-2-carboxylic acid

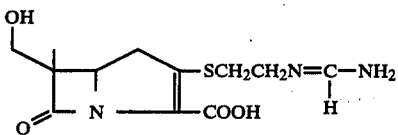

Compound 9 from Example 12-Step K (517 mg) is dissolved in pH 7 0.1 N phosphate buffer (25 ml) and cooled in an ice bath with magnetic stirring. The solution is adjusted to pH 8.5 using 2.5 N sodium hydroxide solution dispensed from an automatic burette. While maintaining a pH of 8.5, methyl formimidate hydrochloride (711 mg) is added portionwise over 2–3 minutes. After an additional 10 minutes, the pH of the solution is brought to 7.0 using 2.5 N hydrochloric acid. The solution is chromatographed on a column of XAD-2 resin (150 cc) which is eluted with water. The N-formimidoyl derivative is eluted and lyophilized.

Following the procedure of Example 33, enhanced product isolation is achieved when the XAD-2 column is replaced by an otherwise equivalent column of Dowex 50-X4 (Na+ cycle, 200–400 mesh).

Amidine embodiments of the present invention, such as that illustrated in Example 33, represent a preferred class. With reference to the generic representation of the compounds of the present invention (Structure I, above), such embodiments are possible when the radical —SR⁸ bears an amino functional group. The preparation of amidine and amidine-like species is fully described in co-pending, commonly assigned U.S. Pat. application Ser. No. 852,425 (filed Nov. 17, 1977), now U.S. Pat. No. 4,194,047, which application is incorporated herein by reference to the extent that it describes the preparation of amidine and amidine-like derivatives from species of the present invention which carry an amino group on —SR⁸.

EXAMPLE 34

Preparation of the N-Acetimidoyl derivative of 3-(2-aminoethylthio)-6-methyl-6-(hydroxymethyl)-7-oxo-1-azabicyclo[3.2.0]hept-2-ene-2-carboxylic acid

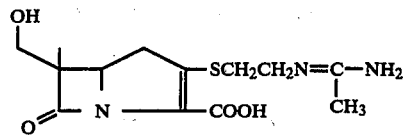

Compound 9 from Example 12, Step K (190 mg) is dissolved in pH 7 0.1 N phosphate buffer (13 ml) and cooled in an ice bath with magnetic stirring. The solution is adjusted to pH 8.5 using 2.5 N sodium hydroxide solution dispensed from an automatic burette. While maintaining a pH of 8.5, ethyl acetimidate hydrochloride (400 mg) is added portionwise over a few minutes. After an additional 40 minutes the solution is adjusted to pH 7.0 with 2.5 N hydrochloric acid. The solution is then chromatographed on Dowex 50-X8 resin (250 cc, Na+ cycle, 100–200 mesh) and is eluted with water. The N-acetimidoyl derivative is eluted and lyophilized.

EXAMPLE 35

Preparation of Silylated 3-(2-aminoethylthio)-6-methyl-6-(hydroxymethyl)-7-oxo-1-azabicyclo[3.2.0]hept-2-ene-2-carboxylic acid

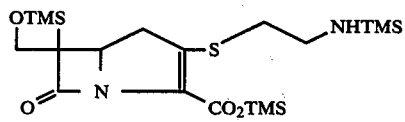

Compound 9 from Example 12, Step K (80.0 mg) is suspended in 40 ml tetrahydrofuran (THF) under a N₂ atmosphere and is concentrated to 10 ml; hexamethyldisilazane (1.0 ml) and trimethylchlorosilane (300 μl) is added. The mixture is reacted for 20 mins. at 25° C. with vigorous stirring. The suspension is then centrifuged to remove ammonium chloride. The supernatant is evaporated to provide the title compound under a nitrogen stream for future reaction.

EXAMPLE 36

Preparation of the N-Piperidin-1-yl Methylene Derivative of 3-(2-aminoethylthio)-6-methyl-6-(hydroxymethyl)-7-oxo-1-azabicyclo[3.2.0]hept-2-ene-2-carboxylic acid

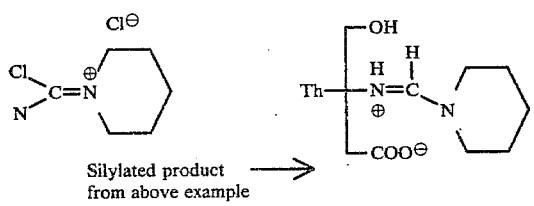

Silylated product ⟶
from above example

Compound 9 from Example 12, Step K (57 mg., 162 μmol) is silylated according to the procedure previously described. The silylated antibiotic is dissolved in methylene chloride (6 cc) in a septum stoppered flask under positive nitrogen pressure and cooled in a dry iceacetone bath. To the magnetically stirred solution is added a solution (180 μl) of triethylamine (644 μmol) in methylene chloride. This is followed by the addition of a solution of chloropiperidinomethylium chloride (67 mg, 405 μmol) in methylene chloride (465 μl). After 1 hour in the dry ice bath, the reaction solution is rapidly added to a tetrahydrofuran -pH 7, 0.1 N phosphate buffer (1:1) solution (50 ml). The mixture is then concentrated under vacuum to 10 ml to give a homogeneous solution. The solution is washed twice with ethyl acetate (2×5 ml) and ether (2×5 ml) and briefly pumped under vacuum. This aqueous solution is then chromatographed on an XAD-2 resin column (60 ml bed). The product is eluted in 10% aqueous tetrahydrofuran (following water elution) to give the captioned product.

EXAMPLE 37

Preparation of the N'-Tert-Butyl-N-Formimidoyl derivative of 3-(2-aminoethylthio)-6-methyl-6-(hydroxymethyl)-7-oxo-1-azabicyclo[3.2.0]hept-2-ene-2-carboxylic acid

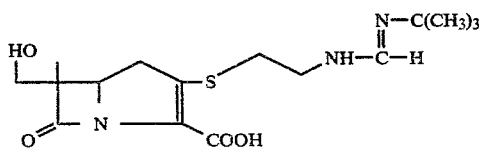

Compound 9 from Example 12, Step K (105 mg) is dissolved in pH 7 0.1 N phosphate buffer (5 ml) and to this is added a solution of ethyl N-tert-butyl formimidate (290 mg) in tetrahydrofuran (1 ml). The pH of the solution is adjusted to and maintained at 8.5 using an autoburette dispensing 1 N NaOH. After 30 minutes, the pH is adjusted to 7.0 with 2.5 N HCl. The solution is chromatographed on an ice water jacketed column of Dowex 50-X4 resin (53 cc, Na⁺ cycle, 200-400 mesh) and eluted with deionized water. The fractions containing the title product are combined and lyophilized.

EXAMPLE 38

Preparation of 8-oxo-2,2-dimethyl-7-ethyl-3-oxa-1-azabicyclo[4.2.0]octane

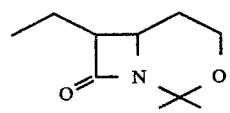

Following the procedure described for the preparation of 8-oxo-3-oxa-2,2-dimethyl-7α-isopropyl-1-azabicyclo[4.2.0]octane from 8-oxo-3-oxa-2,2-dimethyl-1-azabicyclo[4.2.0]octane (Example 4a, above) and using ethyl iodide instead of isopropyl iodide there is obtained 8-oxo-2,2-dimethyl-7-ethyl-3-oxa-1-azabicyclo[4.2.0]octane

EXAMPLE 39

Preparation of 3-(2-aminoethylthio)-6-ethyl-7-oxo-1-azabicyclo[3.2.0-]hept-2-ene-2-carboxylic acid

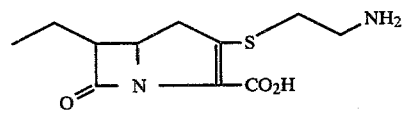

Following the procedures described in Example 7 followed by Example 12-Steps A–K except that in Example 7 an equivalent amount of 8-oxo-2,2-dimethyl-7-ethyl-3-oxa-1-azabicyclo[4.2.0]octane rather than the 2,2,7-trimethyl species is taken, the title compound is obtained.

EXAMPLE 40

Preparation of the N-formimidoyl derivative of 3-(2-aminoethylthio)-6-ethyl-7-oxo-1-azabicyclo[3.2.0-]hept-2-ene-2-carboxylic acid

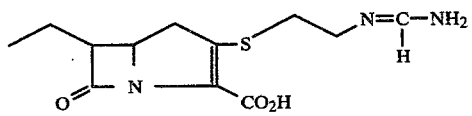

Following the procedure described in Example 33 except that the equivalent amount of 3-(2-aminoethylthio)-6-ethyl-7-oxo-1-azabicyclo[3.2.0]hept-2-ene-2-carboxylic acid rather than Compound 9 is taken, the title compound is obtained.

EXAMPLE 41

Preparation of 3-ethyl-1-(t-butyldimethylsilyl)-4-vinyl-2-azetidinone

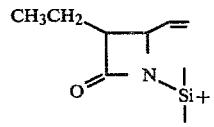

Following the procedure for the preparation of 8-oxo-2,2-dimethyl-7α-isopropyl-3-oxa-1-azabicyclo[4.2.0]octane (Example 4b, above), except that an equivalent amount of 1-(t-butyl-dimethylsilyl)-4-vinyl-2-azetidinone is substituted for the 8-oxo-2,2-dimethyl-3-oxa-1-azabicyclo[4.2.0]octane of Example 4b and using ethyl iodide instead of isopropyl iodide, the title compound is obtained.

EXAMPLE 42

Preparation of 3-ethyl-4-[2-(2-p-nitrobenzyloxycarbonylamino)ethylthio)vinyl]-2-azetidinone

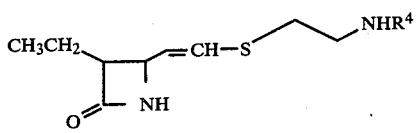

Following the procedures in Example 13-Steps D–F except that an equivalent amount of 3-ethyl-1-(t-butyl-dimethylsilyl)-4-vinyl-2-azetidinone is used in place of Compound 26 of Example 13-Step D, the title compound is obtained.

EXAMPLE 43

Preparation of Pharmaceutical Compositions

One such unit dosage form consists in mixing 3-(2-aminoethylthio)-6-hydroxymethyl-7-oxo-1-azabicyclo[3.2.0]hept-2-ene-2-carboxylic acid with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| 3-(2-aminoethylthio)-6-hydroxymethyl-7-oxo-1-azabicyclo[3.2.0]hept-2-ene-2-carboxylic acid | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| 3-(2-aminoethylthio)-6-hydroxymethyl-7-oxo-1-azabicyclo[3.2.0]hept-2-ene-2-carboxylic acid | 500 mg. |
| Diluent: Sterile Water for Injection | 2 cc. |
| OPTHALMIC SOLUTION | |

| -continued | |
|---|---|
| | PER TABLET |
| 3-(2-aminoethylthio)-6-hydroxymethyl-7-oxo-azabicyclo[3.2.0]hept-2-ene-2-carboxylic acid | 100 mg. |
| Hydropropylmethyl Cellulose | 5 mg. |
| Sterile Water | to 1 ml. |
| OTIC SOLUTION | |
| 3-(2-aminoethylthio)-6-hydroxymethyl-7-oxo-1-azabicyclo[3.2.0]hept-2-ene-2-carboxylic acid | 100 mg. |
| Benzalkonium chloride | 0.1 mg. |
| Sterile Water | to 1 ml. |
| TOPICAL OINTMENT | |
| 3-(2-aminoethylthio)-6-hydroxymethyl-7-oxo-1-azabicyclo[3.2.0]hept-2-ene-2-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, genatmicin, neomycin, colistin and kanamycin, or with other therapeutic agents such as probenecid.

Incorporation by Reference

The compounds of the present invention may also be prepared by the processes disclosed and claimed in the three (3) following, co-pending, commonly assigned, U.S. Patent Applications of Christensen, Ratcliffe and Salzmann. To the extent that these applications define $R^6$, $R^7$, and $R^8$ of Structure I and to the extent that they describe processes for the synthesis of I, they are hereby incorporated by reference.

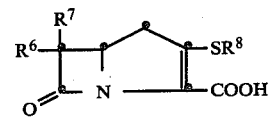

(1) Process for the Preparation of 1-Carbapenems and Intermediates via 4-Allylazetidinone; U.S. Patent Application Ser. No. 134,408 filed Mar. 27, 1980 now abandoned.
(2) Process for the Preparation of 1-Carbapenems and Intermediates via Trithioorthoacetates; U.S. Patent Application Ser. No. 134,396 filed Mar. 27, 1980 now U.S. Pat. No. 4,309,346.
(3) Process for the Preparation of 1-Carbapenems and Intermediates via Sily-Substituted Dithioacetals; U.S. Patent Application Ser. No. 134,397 filed Mar. 27, 1980 now abandoned.

Also incorporated by reference is Belgian Pat. No. 848,545 (which corresponds to co-pending, commonly assigned U.S. Ser. No. 852,425 filed Nov. 17, 1977, now U.S. Pat. No. 4,194,047 issued Mar. 18, 1980). This patent discloses and claims processes for converting the natural product thienamycin to certain amino derivatives:

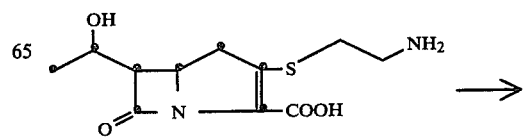

-continued

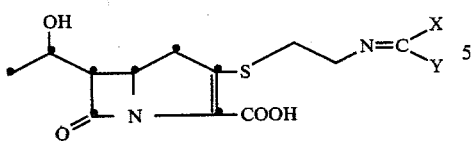

The process disclosed in the cited Belgian Patent is also suitable to prepare preferred, antibiotic embodiments of the present invention (Structure I′, see below). The applicability of the process arises from the presence of an amino group on previously defined side chain —$SR^8$ of the compounds of the present invention, Structure I, thus:

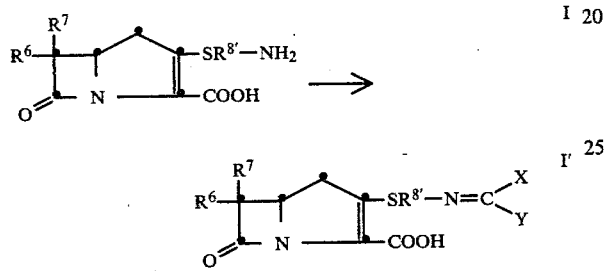

wherein: —$SR^{8'}$—$NH_2$=—$SR^8$; that is, the symbol —$SR^{8'}$—$NH_2$ indicates, and is specific to —$SR^8$, above-defined, bearing an amino substituent; preferred values for X and Y include: X=$NH_2$; Y=H, $CH_3$, $NH_2$.

Thus, to the extent that the Belgian Patent describes the amino derivatization process, the generic definition of X and Y and the preferred, above-indicated, amidine and guanidine embodiments, it is hereby incorporated by reference.

What is claimed is:

1. A compound selected from the group consisting of:

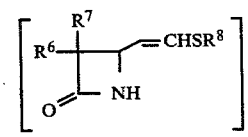

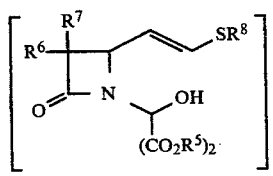

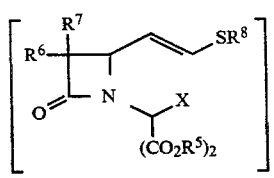

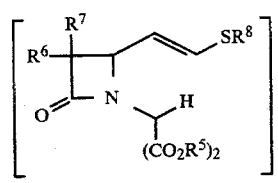

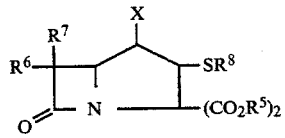

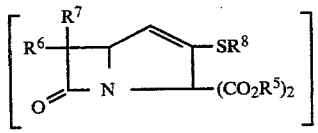

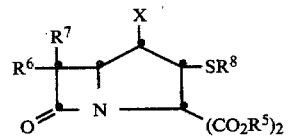

wherein $R^5$ is a removable protecting group or a pharmaceutically acceptable ester moiety; and $R^6$, $R^7$, and $R^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; phenyl, aralkyl, aralkenyl, and aralkynyl wherein the aryl moiety is phenyl and the linear chain has 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms; when $R^7/R^6$ is hydrogen, $R^6/R^7$ is not 1-hydroxyethyl when —$SR^8$ is —$SCH_2CH_2NH_2$; X is chloro or bromo.

2. A compound having the structure:

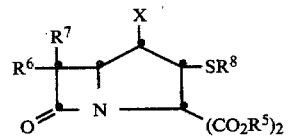

wherein $R^5$ is a removable protecting group or a pharmaceutically acceptable ester moiety $R^6$ is hydrogen or methyl and $R^8$ is selected from the group consisting of:

H, $CH_3$, $(CH_2)_2NH_2$,

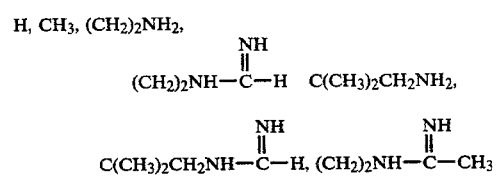

-continued
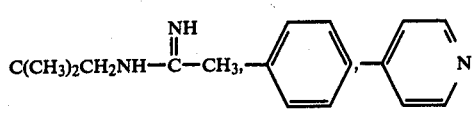
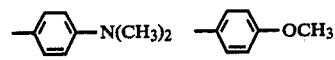
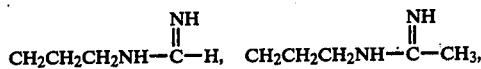
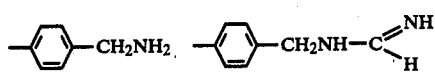
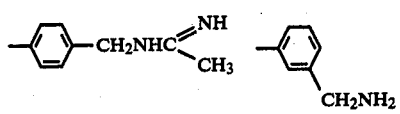
-continued
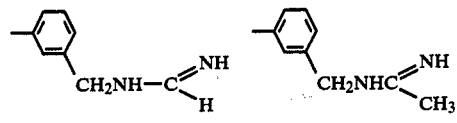
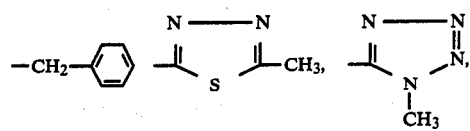
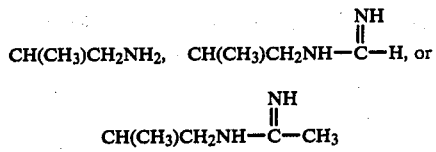
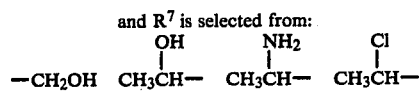
and $R^7$ is selected from:
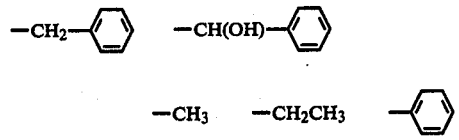
when $R^7/R^6$ is hydrogen, $R^6/R^7$ is not 1-hydroxyethyl when —$SR^8$ is —$SCH_2CH_2NH_2$.
* * * * *